United States Patent [19]
Robertson et al.

[11] Patent Number: 5,814,493
[45] Date of Patent: Sep. 29, 1998

[54] VIRUSES AND EXPRESSION VECTORS CONTAINING LTR SIZE VARIANTS

[75] Inventors: Donald L. Robertson, Orem; Kuhia Loren Fisher, Salt Lake City, both of Utah

[73] Assignee: Brigham Young University, Provo, Utah

[21] Appl. No.: 292,688

[22] Filed: Aug. 18, 1994

[51] Int. Cl.[6] ............................ C12P 19/34; C12N 15/79; C12N 5/10; C07H 21/04
[52] U.S. Cl. ...................................... 435/91.33; 435/320.1; 435/353; 435/357; 536/24.1; 536/24.5
[58] Field of Search ................................ 435/69.1, 172.1, 435/172.3, 240.2, 320.1, 91.1, 91.3, 91.32, 91.33, 91.4, 325, 352, 353, 357; 536/23.1, 24.1, 24.5

[56] References Cited

PUBLICATIONS

Hsu et al., "Mouse Mammary Tumor Virus Proviruses in T–Cell Lymphomas Lack a Negative Regulatory Element in the Long Terminal Repeat", J. of Virol., vol. 62, No. 12, Dec. 1988, pp. 4644–4652.

Mink et al., "The long terminal repant region of the mouse mannary tumour virus contains multiple regulatory elements", Nucleic Acids Res., vol. 18, No. 8, 1990, pp. 2017–2024.

Schmid et al., "Glucocorticoid receptor binds cooperatively, to adjacent recognition sites," EMBO J., vol. 8, No. 8, 1989, pp. 2257–2263.

Lucas et al., "Hormone Response Domains in Gene Transcription", Annu. Rev. Biochem, 1992, vol. 61, pp. 1131–1173.

*Primary Examiner*—David Guzo
*Attorney, Agent, or Firm*—Burns, Doane, Swecker & Mathis, LLP

[57] ABSTRACT

The invention relates to virally-encoded nucleic acid sequences derived from a region 5' to the transcriptional start site of the virus which contain at least one direct repeat of a fragment of a hormone-responsive element. In a preferred embodiment, the virus is murine mammary tumor virus, and the hormone-responsive element is a glucocorticoid responsive element.

43 Claims, 25 Drawing Sheets

MMTV RNA

Linear Double-Stranded DNA

MMTV Integrated DNA

MMTV LTR Regulatory Elements

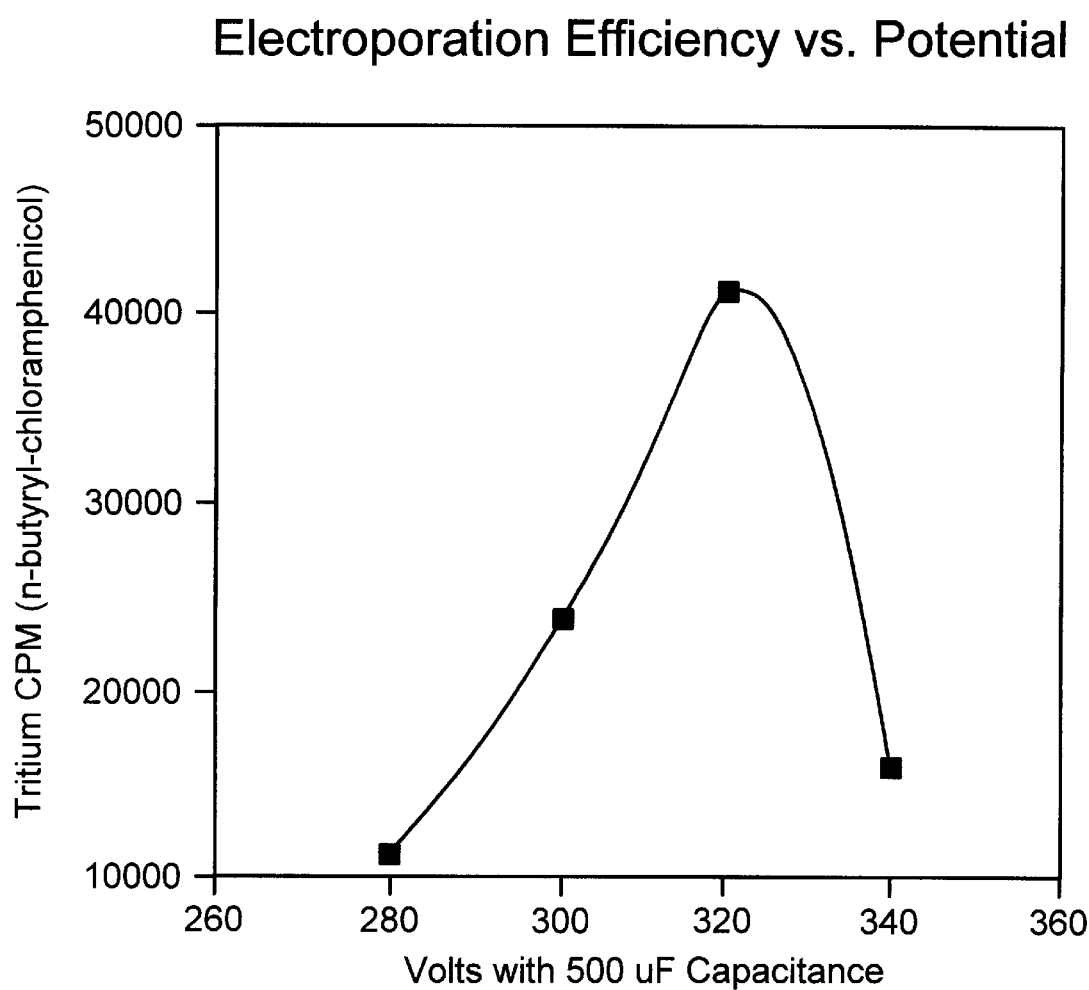

FIG. 10

The 78 Base Pair Repeat

```
         10         20         30         40         50         60
CGGTTCCCAG GGCTTAAGTA AGTTTTTGGT TACAAACTGT TCTTAAAACG AGGATGTGAC
                                   ─────────GR1─────────▶         ◀═
         70         80
TCCTATGTTC TTTTGGAA......▶
────GR4────
```

−441 of C3H LTR relative to +1 transcription site

```
C3H MMTV LTR    1   CGTGAAAGACTCGCCAGAGCTAGACCTCCTTGGTATATGTTGTCTCAAGAAGAAAAAGAC

Variant # 1     1   CGTGAAAGACTCGCCAGAGCTAGACCTCCTTGGTgTATGTTGTCTCAAGAAGAAAAAGAC
Variant # 2     1   CGTGAAAGACTCGCCAGAGCTAGACCTCCTTGGTATATGTT.........GAAAAAGAC
Variant # 3     1   CGTGAAAGACTCGCCAGAGCTAGACCTCCTTGGTgTATGTTGTCTCAAGAAGAAAAAGAC
Variant # 4     1   CGTGAAAGACTCGCCAGAGCTAGACCTCCTTGGTATATGTTGTCTCAAGAAGAAAAAGAC
Variant # 5     1   CGTGAAAGACTCGCCAGAGCTAGACCTCCTTGGTATATGTTGTCTCAAGAAGAAAAAGAC

C3H MMTV LTR    61  GACATGAAACAACAGGTACATGATTATATTTATCTAGGAACAAGAATGCACTTTTGGGGA

Variant # 1     61  GACATGAAACAACAGGTACATGATTATATTTATCTAGGAACAAGAATGCACTTTTGGGGA
Variant # 2     51  GACATGAAACAACAGGTACATGATTATATTTATCTAGGAACAAGAATGCACTTTTGGGGA
Variant # 3     61  GACATGAAACAACAGGTACATGATTATATTTATCTAGGAACAAGAATGCACTTTTGGGGA
Variant # 4     61  GACATGAAACAACAGGTACATGATTATATTTATCTAGGAACAAGAATGCACTTTTGGGGA
Variant # 5     61  GACATGAAACAACAGGTACATGATTATATTTATCTAGGAACAAGAATGCACTTTTGGGGA

C3H MMTV LTR    121 AAGATTTTCCATACCAAGGAGGGGACAGTGGCTAGACTAATAGAACATTATTCTACAAAA

Variant # 1     121 AAGATTTTCCATACCAAGGAGGGGACAGTGGCTAGACTAATAGAACATTATTCTACAAAA
Variant # 2     111 AAGATTTTCCATACCAAGGAGGGGACAGTGGCTAGACTAATAGAACATTATTCTACAAAA
Variant # 3     121 AAGATTTTCCATACCAAGGAGGGGACAGTGGCTAGACTAATAGAACATTATTCTACAAAA
Variant # 4     121 AAGATTTTCCATACCAAGGAGGGGACAGTGGCTAGACTAATAGAACATTATTCTACAAAA
Variant # 5     121 AAGATTTTCCATACCAAGGAGGGGACAGTGGCTAGACTAATAGAACATTATTCTACAAAA

C3H MMTV LTR    181 ACTTATGACATGAGTTATTATAAATAGCCTTTATTGGCCCAACCTTG.............

Variant # 1     181 ACTTATGACATGAGTTATTATAAATAGCCTTTATTGGCCCAACCTTG.............
Variant # 2     171 ACTTATGACATGAGTTATTATAAATAGCCTTTATTGGCCCAACCTTG.............
Variant # 3     181 ACTTATGACATGAGTTATTATAAATAGCCTTTATTGGCCCAACCTTG.............
Variant # 4     180 ACTTATGACATGAGTTATTATAAATAGCCTTTATTGGCCCAACCTTGCGGTTCCCAGGGC
Variant # 5     180 ACTTATGACATGAGTTATTATAAATAGCCTTTATTGGCCCAACCTTGCGGTTCCCAGGGC
                                                                    <-----------

C3H MMTV LTR        ............................................................

Variant # 1         ............................................................
Variant # 2         ............................................................
Variant # 3         ............................................................
Variant # 4     240 TTAGTAAGTTTTTGGTTACAAACTGTTCTTAAAACGAGGATGTGACTCCTATGTTCTTTG
Variant # 5     240 TTAGTAAGTTTTTGGTTACAAACTGTTCTTAAAACGAGGATGTGACTCCTATGTTCTTTG
                           GR1                                 GR4
                    ---------- GR1/GR4 Repeat ----------
```

FIG. 11A

```
C3H MMTV LTR            ............................................
Variant # 1    228  ...CGGTTCCCAGGGCTTAAGTAAGTTTTTGGTTACAAACTGTTCTTAAAACGAGGATGT
Variant # 2    218  ...CGGTTCCCAGGGCTTAAGTAAGTTTTTGGTTACAAACTGTTCTTAAAACGAGGATGT
Variant # 3    228  ...CGGTTCCCAGGGCTTAAGTAAGTTTTTGGTTACAAACTGTTCTTAAAACGAGGATGG
Variant # 4    300  GAACGGTTCCCAGGGCTTAAGTAAGTTTTTGGTTACAAACTGTTCTTAAAACGAGGATGT
Variant # 5    300  GAACGGTTCCCAGGGCTTAAGTAAGTTTTTGGTTACAAACTGTTCTTAAAACGAGGATGT
                                                                  GR1
            -- ------------------------ GR1/GR4 Repeat ----------------

C3H MMTV LTR            ............................................
Variant # 1    285  GACTCCTATGTTCTTTTGGAACGGTTCCCAGGGCTTAAGTAAGTTTTTGGTTACAAACTG
Variant # 2    275  GACTCCTATGTTCTTTTGGAACGGTTCCCAGGGCTTAAGTAAGTTTTTGGTTACAAACTG
Variant # 3    285  GACTCCTATGTTCTTTTGGAACGGTTCCCAGGGCTTAAGTAAGgTTTTGGTTACAAACTG
Variant # 4    360  GACTCCTATGTTCTTTTGGAACGGTTCCCAGGGCTTAAGTAAGTTTTTGGTTACAAACTG
Variant # 5    360  GACTCCTATGTTCTTTTGGAACGGTTCCCAGGGCTTAAGTAAGTTTTTGGTTACAAACTG
                        GR4                                        GR1

--------------------><------------ GR1/GR4 Repeat-----------

C3H MMTV LTR   228  ................................CGGTTCCCAGGGCTTAAGTAA
Variant # 1    345  TTCTTAAAACGAGGATGTGACTCCTATGTTCTTTTGGAACGGTTCCCAGGGCTTAAGTAA
Variant # 2    335  TTCTTAAAACGAGGATGTGACTCCTATGTTCTTTTGGAACGGTTCCCAGGGCTTAAGTAA
Variant # 3    342  TTCTTAAAACGAGGATGTGACTCCTATGTTCTTTTGGAACGGTTCCCAGGGCTTAAGTAA
Variant # 4    420  TTCTTAAAACGAGGATGTGACTCCTATGTTCTTTTGGAACGGTTCCCAGGGCTTAAGTAA
Variant # 5    420  TTCTTAAAACGAGGATGTGACTCCTATGTTCTTTTGGAACGGTTCCCAGGGCTTAAGTAA
                        GR1              GR4

----------------------------------------><-------------------

C3H MMTV LTR   249  GTTTTTGGTTACAAACTGTTCTTAAAACGAGGATGTGAGACAAGTGGTTTCCTGACTTGG
Variant # 1    405  GTcTTTGGTTACAAACTGTTCTTAAAACGAGGATGTGAGACAAGTGGTTTCCTGACTTGG
Variant # 2    394  GTTTTTGGTTACAAACTGTTCTTAAAACGAGGATGTGA......................
Variant # 3    402  GTTTTTGGTTACAAACTGTTCTTAAAACGAGGATGTGAGACAAGTGGTTTCCTGACTTGG
Variant # 4    480  GTTTTTGGTTACAAACTGTTCTTAAAACGAGGATGTGAGACAAGTGGTTTCCTGACTTGG
Variant # 5    480  GTTTTTGGTTACAAACTGTTCTTAAAACGAGGATGTGAGACAAGTGGTTTCCTGACTTGG
                              GR1
            ------------------------ Normal 4-element GRE ---------------

C3H MMTV LTR   309  TTTGGTATCAAAGGTTCTGATCTGAGCTCTGAGTGTTCTATTTTCCTATGTTCTTTTGGA
Variant # 1    465  TTTGGTATCAAAGGTTCTGATCTGAGCTCTGAGTGTTCTATTTTCCTATGTTCTTTTGGA
Variant # 2    435  ............................................CTCCTATGTTCTTTTGGA
Variant # 3    462  TTTGGTATCAAAGGTTCTGATCTGAGCTCTGAGTGTTCTATTTTCCTATGTTCTTTTGGA
Variant # 4    540  TTTGGTATCAAAGGTTCTGATCTGAGCTCTGAGTGTTCTATTTTCCTATGTTCTTTTGGA
Variant # 5    540  TTTGGTATCAAAGGTTCTGATCTGAGCTCTGAGTGTTCTATTTTCCTATGTTCTTTTGGA
                        GR2                GR3              GR4

-------------- Normal 4-element GRE ------------------------>
```

FIG. 11B

| | | |
|---|---|---|
| C3H MMTV LTR | 369 | ATTTATCCAAATCTTATGTAAATGCTTATGTAAACCAAGATATAAAAGAGTGCTGATTTT |
| Variant # 1 | 525 | ATTTATCCAAATCTTATGTAAATGCTTATGTAAACCAAGATATAAAAGAGTGCTGATTTT |
| Variant # 2 | 453 | ATTTATCCAAATCTTATGTAAATGCTTATGTAAACCAAGATATAAAAGAGTGCTGATTTT |
| Variant # 3 | 522 | ATTTATCCAAATCTTATGTAAATGCTTATGTAAACCAAGATATAAAAGAGTGCTGATTTT |
| Variant # 4 | 600 | ATTTATCCAAATCTTATGTAAATGCTTATGTAAACCAAGATATAAAAGAGTGCTGATTTT |
| Variant # 5 | 600 | ATTTATCCAAATCTTATGTAAATGCTTATGTAAACCAAGATATAAAAGAGTGCTGATTTT |
| | | |
| C3H MMTV LTR | 429 | TTTGAGTAAACTTGCAACA... |
| | | |
| Variant # 1 | 585 | TTTGAGTAAACTTGCAACA... |
| Variant # 2 | 513 | TTTGAGTAAACTTGCAACA... |
| Variant # 3 | 582 | TTTGAGTAAACTTGCAACA... |
| Variant # 4 | 660 | TTTGAGTAAACTTGCAACA... |
| Variant # 5 | 660 | TTTGAGTAAACTTGCAACA... |

+1 start site of RNA transcription

FIG. 11C

Efficiency Comparison of Promoters Inducing CAT Activity pCAT®-Control and pCAT®-Basic by Promega Corp
pCAT®-Control contains constitutive SV40 promoters and enhancers
pCAT®-Basic contains no promoter or enhancers
Variant MMTV LTR's were inserted into pCAT®-Basic C3H MMTV LTR wild-type (SEQ ID NO: 9)

```
         10         20         30         40         50         60         70
ATGCCGCGCC TGCAGCAGAA ATGGTTGAAC TCCCGAGAGT GTCCTACACC TAGGGGAGAA GCAGCCAAGG
         80         90        100        110        120        130        140
GGTTGTTTCC CACCAAGGAC GACCCGTCTG CGCACAAACG GGTGAGCCCA TCAGACAAAG ACATATTCAT
        150        160        170        180        190        200        210
TCTCTGCTGC AAACTTGGCA TAGCTCTGCT TTGCCTGGGG CTATTGGGGG AAGTTGCGGT TCGTGCTCGC
        220        230        240        250        260        270        280
AGGGCTCTCA CCCTTGACTC TTTTAATAGC TCTTCTGTGC AAGATTACAA TCTAAACAAT TCGGAGAACT
        290        300        310        320        330        340        350
CGACCTTCCT CCTGAGGCAA GGACCACAGC CAACTTCCTC TTACAAGCCG CATCGATTTT GTCCTTCAGA
        360        370        380        390        400        410        420
AATAGAAATA AGAATGCTTG CTAAAAATTA TATTTTTACC AATAAGACCA ATCCAATAGG TAGATTATTA
        430        440        450        460        470        480        490
GTTACTATGT TAAGAAATGA ATCATTATCT TTTAGTACTA TTTTTACTCA AATTCAGAAG TTAGAAATGG
        500        510        520        530        540        550        560
GAATAGAAAA TAGAAAGAGA CGCTCAACCT CAATTGAAGA ACAGGTGCAA GGACTATTGA CCACAGGCCT
        570        580        590        600        610        620        630
AGAAGTAAAA AAGGGAAAAA AGAGTGTTTT TGTCAAAATA GGAGACAGGT GGTGGCAACT AGGGACTTAT
        640        650        660        670        680        690        700
AGGGGACCTT ACATCTACAG ACCAACAGAT GCCCCCTTAC CATATACAGG AAGATATGAC TTAAATTGGG
        710        720        730        740        750        760        770
ATAGGTGGGT TACAGTCAAT GGCTATAAAG TGTTATATAG ATCCCTCCCT TTTCGTGAAA GACTCGCCAG
        780        790        800        810        820        830        840
AGCTAGACCT CCTTGGTGTA TGTTGTCTCA AGAAGAAAAA GACGACATGA AACAACAGGT ACATGATTAT
        850        860        870        880        890        900        910
ATTTATCTAG GAACAGGAAT GCACTTTTGG GGAAAGATTT TCCATACCAA GGAGGGGACA GTGGCTGGAC
        920        930        940        950        960        970        980
TAATAGAACA TTATTCTCCA AAAACTTATG GCATGAGTTA TTATGAATAG CCTTTATTGG CCCAACCTTG
        990       1000       1010       1020       1030       1040       1050
CGGTTCCCAG GGCTTAAGTA AGTTTTTGGT TACAAACTGT TCTTAAAACG AGGATGTGAG ACAAGTGGTT
       1060       1070       1080       1090       1100       1110       1120
TCCTGACTTG GTTTGGTATC AAAGGTTCTG ATCTGAGCTC TGAGTGTTCT ATTTTCCTAT GTTCTTTTGG
       1130       1140       1150       1160       1170       1180       1190
AATTTATCCA AATCTTATGT AAATGCTTAT GTAAACCAAG ATATAAAAGA GTGCTGATTT TTTTGAGTAA
       1200       1210       1220       1230       1240       1250       1260
ACTTGCAACA GTTCCTAACA TTCACCTCTT GTGTGTTTGT GTCTGTTCGC CATCCCGTCT CCGCTCGTCA
```

FIG. 17A

```
     1270       1280       1290       1300       1310       1320       1330
CTTATCCTTC ACTTTCCTGC GGGTCCCCCC GCAGACCCCG GCGACCTCAG GTCGGCCGAC TGCGGCAGCT
     1340       1350       1360       1370       1380       1390       1400
GGCGCCCGAA CAGGGACCCC TCGGATAAGT GACCCTTGTC TCTATTTCTA CTATTTGGTG TTTGTCTTGT
     1401       1420       1430       1440       1450       1460
ATTGTCTCTT TCTTGTCTTT CTATCATCAC AAGAGCGGAA CGGACTCACC ATAGGGAGCT GCAG
```

C3H MMTV LTR Variant No. 1 (SEQ ID NO: 10)

```
       10         20         30         40         50         60         70
ATGCCGCGCC TGCAGCAGAA ATGGTTGAAC TCCCGAGAGT GTCCTACACC TAGGGGAGAA GCAGCCAAGG
       80         90        100        110        120        130        140
GGTTGTTTCC CACCAAGGAC GACCCGTCTG CGCACAAACG CGCACAAACG GGTGAGCCCA ACATATTCAT
      150        160        170        180        190        200        210
TCTCTGCTGC AAACTTGGCA TAGCTCTGCT TTGCCTGGGG CTATTGGGGG AAGTTGCGGT TCGTGCTCGC
      220        230        240        250        260        270        280
AGGGCTCTCA CCCTTGACTC TTTTAATAGC TCTTCTGTGC AAGATTACAA TCTAAACAAT TCGGAGAACT
      290        300        310        320        330        340        350
CGACCTTCCT CCTGAGGCAA GGACCACAGC CAACTTCCTC TTACAAGCCG CATCGATTTT GTCCTTCAGA
      360        370        380        390        400        410        420
AATAGAAATA AGAATGCTTG CTAAAAATTA TATTTTTACC AATAAGACCA ATCCAATAGG TAGATTATTA
      430        440        450        460        470        480        490
GTTACTATGT TAAGAAATGA ATCATTATCT TTTAGTACTA TTTTTACTCA AATTCAGAAG TTAGAAATGG
      500        510        520        530        540        550        560
GAATAGAAAA TAGAAAGAGA CGCTCAACCT CAATTGAAGA ACAGGTGCAA GGACTATTGA CCACAGGCCT
      570        580        590        600        610        620        630
AGAAGTAAAA AAGGGAAAAA AGAGTGTTTT TGTCAAAATA GGAGACAGGT GGTGGCAACT AGGGACTTAT
      640        650        660        670        680        690        700
AGGGGACCTT ACATCTACAG ACCAACAGAT GCCCCCTTAC CATATACAGG AAGATATGAC TTAAATTGGG
      710        720        730        740        750        760        770
ATAGGTGGGT TACAGTCAAT GGCTATAAAG TGTTATATAG ATCCCTCCCT TTTCGTGAAA GACTCGCCAG
      780        790        800        810        820        830        840
AGCTAGACCT CCTTGGTGTA TGTTGTCTCA AGAAGAAAAA GACGACATGA AACAACAGGT ACATGATTAT
      850        860        870        880        890        900        910
ATTTATCTAG GAACAGGAAT GCACTTTTGG GGAAAGATTT TCCATACCAA GGAGGGGACA GTGGCTAGAC
      920        930        940        950        960        970        980
TAATAGAACA TTATTCTACA AAAACTTATG ACATGAGTTA TTATAAATAG CCTTTATTGG CCCAACCTTA
      990       1000       1010       1020       1030       1040       1050
GACGGTTCCC AGGGCTTAAG TAAGTTTTTG GTTACAAACT GTTCTTAAAA CGAGGATGTG ACTCCTATGT
```

FIG. 17B

```
     1060        1070        1080        1090        1100        1110        1120
TCTTTTGAAC  GGTTCCCAGG  GCTTAAGTAA  GTTTTTGGTT  ACAAACTGTT  CTTAAAACGA  GGATGTGACT 1130        1140        1150        1160        1170        1180        1190
CCTATGTTCT  TTTGGAACGG  TTCCCAGGGC  TTAAGTAAGT  CTTTGGTTAC  AAACTGTTCT  TAAAACGAGG 1200        1210        1220        1230        1240        1250        1260
ATGTGAGACA  AGTGGTTTCC  TGACTTGGTT  TGGTATCAAA  GGTTCTGATC  TGAGCTCTGA  GTGTTCTATT 1270        1280        1290        1300        1310        1320        1330
TTCCTATGTT  CTTTTGGAAT  TTATCCAAAT  CTTATGTAAA  TGCTTATGTA  AACCAAGATA  TAAAAGAGTG 1340        1350        1360        1370        1380        1390        1400
CTGATTTTTT  TGAGTAAACT  TGCAACAGTT  CCTAACATTC  ACCTCTTGTG  TGTTTGTGTC  TGTTCGCCAT 1410        1420        1430        1440        1450        1460        1470
CCCGTCTCCG  CTCGTCACTT  ATCCTTCACT  TTCCTGCGGG  TCCCCCCGCA  GACCCCGGCG  ACCTCAGGTC 1480        1490        1500        1510        1520        1530        1540
GGCCGACTGC  GGCAGCTGGC  GCCCGAACAG  GGACCCCTCG  GATAAGTGAC  CCTTGTCTCT  ATTTCTACTA 1550        1560        1570        1580        1590        1600        1610
TTTGGTGTTT  GTCTTGTATT  GTCTCTTTCT  TGTCTTTCTA  TCATCACAAG  AGCGGAACGG  ACTCACCATA

1620
GGGAGCTGCA  G
```

C3H MMTV LTR Variant No. 2 (SEQ ID NO: 11)

```
       10          20          30          40          50          60          70
ATGCCGCGCC  TGCAGCAGAA  ATGGTTGAAC  TCCCGAGAGT  GTCCTACACC  TAGGGGAGAA  GCAGCCAAGG 80          90         100         110         120         130         140
GGTTGTTTCC  CACCAAGGAC  GACCCGTCTG  CGCACAAACG  GGTGAGCCCA  TCAGACAAAG  ACATATTCAT 150         160         170         180         190         200         210
TCTCTGCTGC  AAACTTGGCA  TAGCTCTGCT  TTGCCTGGGG  CTATTGGGGG  AAGTTGCGGT  TCGTGCTCGC 220         230         240         250         260         270         280
AGGGCTCTCA  CCCTTGACTC  TTTTAATAGC  TCTTCTGTGC  AAGATTACAA  TCTAAACAAT  TCGGAGAACT 290         300         310         320         330         340         350
CGACCTTCCT  CCTGAGGCAA  GGACCACAGC  CAACTTCCTC  TTACAAGCCG  CATCGATTTT  GTCCTTCAGA 360         370         380         390         400         410         420
AATAGAAATA  AGAATGCTTG  CTAAAAATTA  TATTTTTACC  AATAAGACCA  ATCCAATAGG  TAGATTATTA 430         440         450         460         470         480         490
GTTACTATGT  TAAGAAATGA  ATCATTATCT  TTTAGTACTA  TTTTTACTCA  AATTCAGAAG  TTAGAAATGG 500         510         520         530         540         550         560
GAATAGAAAA  TAGAAAGAGA  CGCTCAACCT  CAATTGAAGA  ACAGGTGCAA  GGACTATTGA  CCACAGGCCT
```

FIG. 17C

```
       570        580        590        600        610        620        630
AGAAGTAAAA AAGGGAAAAA AGAGTGTTTT TGTCAAAATA GGAGACAGGT GGTGGCAACT AGGGACTTAT 640        650        660        670        680        690        700
AGGGGACCTT ACATCTACAG ACCAACAGAT GCCCCCTTAC CATATACAGG AAGATATCAG TTAAATTGGG 710        720        730        740        750        760        770
ATAGGTGGGT TACAGTCAAT GGCTATAAAG TGTTATATAG ATCCCTCCCT TTTCGTGAAA GACTCGCCAG 780        790        800        810        820        830        840
AGCTAGACCT CCTTGGTGTA TGTTGAAAAA GACGACATGA AACAACAGGT ACATGATTAT ATTTATCTAG 850        860        870        880        890        900        910
GAACAGGAAT GCACTTTTGG GGAAAGATTT TCCATACCAA GGAGGGGACA GTGGCTGGAC TAATAGAACA 920        930        940        950        960        970        980
TTATTCTCCA AAAACTTATG GCATGAGTTA TTATGAATAG CCTTTATTGG CCCAACCTTG CGGTTCCCAG 990       1000       1010       1020       1030       1040       1050
GGCTTAAGTA AGTTTTTGGT TACAAACTGT TCTTAAAACG AGGATGTGAC TCCTATGTTC TTTTGGAACG 1060       1070       1080       1090       1100       1110       1120
GTTCCCAGGG CTTAAGTAAG TTTTTGGTTA CAAACTGTTC TTAAAACGAG GATGTGACTC CTATGTTCTT 1130       1140       1150       1160       1170       1180       1190
TTGGAACGGT TCCCAGGGCT TAAGTAAGTT TTTGGTTACA AACTGTTCTT AAAACGAGGA TGTGACTCCT 1200       1210       1220       1230       1240       1250       1260
ATGTTCTTTT GGAATTTATC CAAATCTTAT GTAAATGCTT ATGTAAACCA AGATATAAAA GAGTGCTGAT 1270       1280       1290       1300       1310       1320       1330
TTTTTTGAGT AAACTTGCAA CAGTTCCTAA CATTCACCTC TTGTGTGTTT GTGTCTGTTC GCCATCCCGT 1340       1350       1360       1370       1380       1390       1400
CTCCGCTCGT CACTTATCCT TCACTTTCCT GCGGGTCCCC CCGCAGACCC CGGCGACCTC AGGTCGGCCG 1410       1420       1430       1440       1450       1460       1470
ACTGCGGCAG CTGGCGCCCG AACAGGGACC CCTCGGATAA GTGACCCTTG TCTCTATTTC TACTATTTGG 1480       1490       1500       1510       1520       1530       1540
TGTTTGTCTT GTATTGTCTC TTTCTTGTCT TTCTATCATC ACAAGAGCGG AACGGACTCA CCATAGGGAG

CTGCAG

C3H MMTV LTR Variant No. 3 (SEQ ID NO: 12)

10         20         30         40         50         60         70
ATGCCGCGCC TGCAGCAGAA ATGGTTGAAC TCCCGAGAGT GTCCTACACC TAGGGGAGAA GCAGCCAAGG 80         90        100        110        120        130        140
GGTTGTTTCC CACCAAGGAC GACCCGTCTG CGCACAAACG GGTGAGCCCA TCAGACAAAG ACATATTCAT
```

FIG. 17D

```
          150         160        170        180        190        200        210
TCTCTGCTGC  AAACTTGGCA  TAGCTCTGCT  TTGCCTGGGG  CTATTGGGGG  AAGTTGCGGT  TCGTGCTCGC 220         230        240        250        260        270        280
AGGGCTCTCA  CCCTTGACTC  TTTTAATAGC  TCTTCTGTGC  AAGATTACAA  TCTAAACAAT  TCGGAGAACT 290         300        310        320        330        340        350
CGACCTTCCT  CCTGAGGCAA  GGACCACAGC  CAACTTCCTC  TTACAAGCCG  CATCGATTTT  GTCCTTCAGA 360         370        380        390        400        410        420
AATAGAAATA  AGAATGCTTG  CTAAAAATTA  TATTTTTACC  AATAAGACCA  ATCCAATAGG  TAGATTATTA 430         440        450        460        470        480        490
GTTACTATGT  TAAGAAATGA  ATCATTATCT  TTTAGTACTA  TTTTTACTCA  AATTCAGAAG  TTAGAAATGG 500         510        520        530        540        550        560
GAATAGAAAA  TAGAAAGAGA  CGCTCAACCT  CAATTGAAGA  ACAGGTGCAA  GGACTATTGA  CCACAGGCCT 570         580        590        600        610        620        630
AGAAGTAAAA  AAGGGAAAAA  AGAGTGTTTT  TGTCAAAATA  GGAGACAGGT  GGTGGCAACT  AGGGACTTAT 640         650        660        670        680        690        700
AGGGGACCTT  ACATCTACAG  ACCAACAGAT  GCCCCCTTAC  CATATACAGG  AAGATATGAC  TTAAATTGGG 710         720        730        740        750        760        770
ATAGGTGGGT  TACAGTCAAT  GGCTATAAAG  TGTTATATAG  ATCCCTCCCT  TTTCGTGAAA  GACTCGCCAG 780         790        800        810        820        830        840
AGCTAGACCT  CCTTGGTGTA  TGTTGTCTCA  AGAAGAAAAA  GACGACATGA  AACAACAGGT  ACATGATTAT 850         860        870        880        890        900        910
ATTTATCTAG  GAACAAGAAT  GCACTTTTGG  GGAAAGATTT  TCCATACCAA  GGAGGGGACA  GTGGCTAGAC 920         930        940        950        960        970        980
TAATAGAACA  TTATTCTACA  AAAACTTATG  ACATGAGTTA  TTATAAATAG  CCTTTATTGG  CCCAACCTTG 990        1000       1010       1020       1030       1040       1050
CGGTTCCCAG  GGCTTAAGTA  AGTTTTGGTT  ACAAACTGTT  CTTAAAACGA  GGATGTGACT  CCTATCTTTT 1060        1070       1080       1090       1100       1110       1120
GGAACGGTTC  CCANGGCTTA  AGTAAGGTTT  TGGTTACAAA  CTGTTCTTAA  AACGAGGATG  TGACTCCTAT 1130        1140       1150       1160       1170       1180       1190
GTTCTTTTGG  AACGGTTCCC  AGGGCTTAAG  TAAGTTTTTG  GTTACAAACG  GTTCTTAAAA  CGAGGATGTG 1200        1210       1220       1230       1240       1250       1260
AGACAAGTGG  TTTCCTGACT  TGGTTTGGTA  TCAAAGGTTC  TGATCTGAGC  TCTGAGTGTT  CTATTTTCCT 1270        1280       1290       1300       1310       1320       1330
ATGTTCTTTT  GGAATTTATC  CAAATCTTAT  GTAAATGCTT  ATGTAAACCA  AGATATAAAA  GAGTGCTGAT 1340        1350       1360       1370       1380       1390       1400
TTTTTTGAGT  AAACTTGCAA  CAGTTCCTAA  CATTCACCTC  TTGTGTGTTT  GTGTCTGTTC  GCCATCCCGT
```

FIG. 17E

```
              1410       1420       1430       1440       1450       1460       1470
         CTCCGCTCGT CACTTATCCT TCACTTTCCT GCAGGTCCCC CCGCAGACCC CGGCGACCTC AGGTCGGCCG
              1480       1490       1500       1510       1520       1530       1540
         ACTGCGGCAG CTGGCGCCCG AACAGGGACC CCTCGGATAA GTGACCCTTG TCTCTATTTC TACTATTTGG
              1550       1560       1570       1580       1590       1600       1610
         TGTTTGTCTT GTATTGTCTC TTTCTTGTCT TTCTATCATC ACAAGAGCGG AACGGACTCA CCATAGGGAG

CTGCAG

C3H MMTV LTR Variant No. 4 (SEQ ID NO: 13)
              10         20         30         40         50         60         70
         ATGCCGCGCC TGCAGCAGAA ATGGTTGAAC TCCCGAGAGT GTCCTACACC TAGGGGAGAA GCAGCCAAGG
              80         90         100        110        120        130        140
         GGTTGTTTCC CACCAAGGAC GACCCGTCTG CGCACAAACG GGTGAGCCCA TCAGACAAAG ACATATTCAT
              150        160        170        180        190        200        210
         TCTCTGCTGC AAACTTGGCA TAGCTCTGCT TTGCCTGGGG CTATTGGGGG AAGTTGCGGT TCGTGCTCGC
              220        230        240        250        260        270        280
         AGGGCTCTCA CCCTTGACTC TTTTAATAGC TCTTCTGTGC AAGATTACAA TCTAAACAAT TCGGAGAACT
              290        300        310        320        330        340        350
         CGACCTTCCT CCTGAGGCAA GGACCACAGC CAACTTCCTC TTACAAGCCG CATCGATTTT GTCCTTCAGA
              360        370        380        390        400        410        420
         AATAGAAATA AGAATGCTTG CTAAAAATTA TATTTTTACC AATAAGACCA ATCCAATAGG TAGATTATTA
              430        440        450        460        470        480        490
         GTTACTATGT TAAGAAATGA ATCATTATCT TTTAGTACTA TTTTTACTCA AATTCAGAAG TTAGAAATGG
              500        510        520        530        540        550        560
         GAATAGAAAA TAGAAAGAGA CGCTCAACCT CAATTGAAGA ACAGGTGCAA GGACTATTGA CCACAGGCCT
              570        580        590        600        610        620        630
         AGAAGTAAAA AAGGGAAAAA AGAGTGTTTT TGTCAAAATA GGAGACAGGT GGTGGCAACT AGGGACTTAT
              640        650        660        670        680        690        700
         AGGGGACCTT ACATCTACAG ACCAACAGAT GCCCCCTTAC CATATACAGG AAGATATGAC TTAAATTGGG
              710        720        730        740        750        760        770
         ATAGGTGGGT TACAGTCAAT GGCTATAAAG TGTTATATAG ATCCCTCCCT TTTCGTGAAA GACTCGCCAG
              780        790        800        810        820        830        840
         AGCTAGACCT CCTTGGTATA TGTTGTCTCA AGAAGAAAAA GACGACATGA AACAACAGGT ACATGATTAT
              850        860        870        880        890        900        910
         ATTTATCTAG GAACAAGAAT GCACTTTTGG GGAAAGATTT CCATACCAAG GAGGGGACAG TGGCTAGACA
```

FIG. 17F

```
           920        930        940        950        960        970        980
     ATAGAACATT ATTCTACAAA AACTTATGAC ATGAGTTATT ATAAATAGCC TTTATTGGCC CAACCTTGCG 990       1000       1010       1020       1030       1040       1050
     GTTCCCAGGG CTTAGTAAGT TTTTGGTTAC AAACTGTTCT TAAAACGAGG ATGTGACTCC TATGTTCTTT 1060       1070       1080       1090       1100       1110       1120
     GGAACGGTTC CCAGGGCTTA AGTAAGTTTT TGGTTACAAA CTGTTCTTAA AACGAGGATG TGACTCCTAT 1130       1140       1150       1160       1170       1180       1190
     GTTCTTTTGG ACGGTTCCCA GGGCTTAAGT AAGTTTTTGG TTACAAACTG TTCTTAAAAC GAGGATGTGA 1200       1210       1220       1230       1240       1250       1260
     CTCCTATGTT CTTTTGGAAC GGTTCCCAGG GCTTAAGTAA GTTTTTGGTT ACAAACTGTT CTTAAAACGA 1270       1280       1290       1300       1310       1320       1330
     GGATGTGAGA CAAGTGGTTT CCTGACTTGG TTTGGTATCA AAGGTTCTGA TCTGAGCTCT GAGTGTTCTA 1340       1350       1360       1370       1380       1390       1400
     TTTTCCTATG TTCTTTTGGA ATTTATCCAA ATCTTATGTA AATGCTTATG TAAACCAAGA TATAAAAGAG 1410       1420       1430       1440       1450       1460       1470
     TGCTGATTTT TTTGAGTAAA CTTGCAACAG TTCCTAACAT TCACCTCTTG TGTGTTTGTG TCTGTTCGCC

1480±      1490       1500       1510       1520       1530       1540
     ATCCCGTCTC CGCTCGTCAC TTATCCTTCA CTTTCCTGCG GGTCCCCCCG CAGACCCCGG CGACCTCAGG 1550       1560       1570       1580       1590       1600       1610
     TCGGCCGACT GCGGCAGCTG GCGCCCGAAC AGGGACCCCT CGGATAAGTG ACCCTTGTCT CTATTTCTAC 1620       1630       1640       1650       1660       1670       1680
     TATTTGGTGT TTGTCTTGTA TTGTCTCTTT CTTGTCTTTC TATCATCACA AGAGCGGAAC GGACTCACCA

1690
     TAGGGAGCTC CAG

C3H MMTV LTR Variant No. 5 (SEQ ID NO: 14)

10         20         30         40         50         60         70
     ATGCCGCGCC TGCAGCAGAA ATGGTTGAAC TCCCGAGAGT GTCCTACACC TAGGGGAGAA GCAGCCAAGG 80         90        100        110        120        130        140
     GGTTGTTTCC CACCAAGGAC GACCCGTCTG CGCACAAACG GGTGAGCCCA TCAGACAAAG ACATATTCAT 150        160        170        180        190        200        210
     TCTCTGCTGC AAACTTGGCA TAGCTCTGCT TTGCCTGGGG CTATTGGGGG AAGTTGCGGT TCGTGCTCGC 220        230        240        250        260        270        280
     AGGGCTCTCA CCCTTGACTC TTTTAATAGC TCTTCTGTGC AAGATTACAA TCTAAACAAT TCGGAGAACT
```

FIG. 17G

```
         290        300        310        320        330        340        350
CGACCTTCCT CCTGAGGCAA GGACCACAGC CAACTTCCTC TTACAAGCCG CATCGATTTT GTCCTTCAGA 360        370        380        390        400        410        420
AATAGAAATA AGAATGCTTG CTAAAAATTA TATTTTTACC AATAAGACCA ATCCAATAGG TAGATTATTA 430        440        450        460        470        480        490
GTTACTATGT TAAGAAATGA ATCATTATCT TTTAGTACTA TTTTTACTCA AATTCAGAAG TTAGAAATGG 500        510        520        530        540        550        560
GAATAGAAAA TAGAAAGAGA CGCTCAACCT CAATTGAAGA ACAGGTGCAA GGACTATTGA CCACAGGCCT 570        580        590        600        610        620        630
AGAAGTAAAA AAGGGAAAAA AGAGTGTTTT TGTCAAAATA GGAGACAGGT GGTGGCAACT AGGGACTTAT 640        650        660        670        680        690        700
AGGGGACCTT ACATCTACAG ACCAACAGAT GCCCCCTTAC CATATACAGG AAGATATGAC TTAAATTGGG 710        720        730        740        750        760        770
ATAGGTGGGT TACAGTCAAT GGCTATAAAG TGTTATATAG ATCCCTCCCT TTTCGTGAAA GACTCGCCAG 780        790        800        810        820        830        840
AGCTAGACCT CCTTGGTATA TGTTGTCTCA AGAAGAAAAA GACGACATGA AACAACAGGT ACATGATTAT 850        860        870        880        890        900        910
ATTTATCTAG GAACAAGAAT GCACTTTTGG GGAAAGATTT CCATACCAAG GAGGGGACAG TGGCTAGACA 920        930        940        950        960        970        980
ATAGAACATT ATTCTACAAA AACTTATGAC ATGAGTTATT ATAAATAGCC TTTATTGGCC CAACCTTGCG 990       1000       1010       1020       1030       1040       1050
GTTCCCAGGG CTTAGTAAGT TTTTGGTTAC AAACTGTTCT TAAAACGAGG ATGTGACTCC TATGTTCTTT 1060       1070       1080       1090       1100       1110       1120
GGAACGGTTC CCAGGGCTTA AGTAAGTTTT TGGTTACAAA CTGTTCTTAA AACGAGGATG TGACTCCTAT 1130       1140       1150       1160       1170       1180       1190
GTTCTTTTGG ACGGTTCCCA GGGCTTAAGT AAGTTTTTGG TTACAAACTG TTCTTAAAAC GAGGATGTGA 1200       1210       1220       1230       1240       1250       1260
CTCCTATGTT CTTTTGGAAC GGTTCCCAGG GCTTAAGTAA GTTTTTGGTT ACAAACTGTT CTTAAAACGA 1270       1280       1290       1300       1310       1320       1330
GGTAGTGAGA CAAGTGGTTT CCTGACTTGG TTTGGTATCA AAGGTTCTGA TCTGAGCTCT GAGTGTTCTA 1340       1350       1360       1370       1380       1390       1400
TTTTCCTATG TTCTTTTGGA ATTTATCCAA ATCTTATGTA AATGCTTATG TAAACCAAGA TATAAAAGAG 1410       1420       1430       1440       1450       1460       1470
TGCTGATTTT TTTGAGTAAA CTTGCAACAG TTCCTAACAT TCACCTCTTG TGTGTTTGTG TCTGTTCGCC 1480       1490       1500       1510       1520       1530       1540
ATCCCGTCTC CGCTCGTCAC TTATCCTTCA CTTTCCTGCG GGTCCCCCCG CAGACCCCGG CGACCTCAGG
```

FIG. 17H

```
      1550       1560       1570       1580       1590       1600       1610
TCGGCCGACT GCGGCAGCTG GCGCCCGAAC AGGGACCCCT CGGATAAGTG ACCCTTGTCT CTATTTCTAC 1620       1630       1640       1650       1660       1670       1680
TATTTGGTGT TTGTCTTGTA TTGTCTCTTT CTTGTCTTTC TATCATCACA AGAGCGGAAC GGACTCACCA

1690
TAGGGAGCTG CAG
```

FIG. 17I

VIRUSES AND EXPRESSION VECTORS CONTAINING LTR SIZE VARIANTS

BACKGROUND OF THE INVENTION
1. Field of the Invention

This invention relates to a method for expressing foreign genes in mammalian cells, and to expression vectors for conducting such expression. Specifically, the invention relates to methods of expression and vectors containing sequences obtained from long terminal repeat (LTR) regions of viruses containing repeat sequences representing portions of a glucocorticoid responsive element.

2. Description of the Related Art

Prokaryotic expression systems have been used to produce eukaryotic proteins, with limited success. Because eukaryotic proteins are often posttranslationally modified as they occur in nature, the lack of appropriate mechanisms for such modification in bacteria often leads to expression of protein which is incorrectly folded, and thus, has little or no biological activity.

Several eukaryotic expression systems have been developed to circumvent this problem, including systems for expression in yeast, expression in insect cells (baculovirus) and systems for expression in mammalian cells which include viral sequences from viruses such as simian virus 40 (SV40), bovine papillomavirus, vaccinia virus, adenovirus, and various retroviruses. However, these systems have met with limited success, as they are not readily induced, and are not generally capable of being induced to high levels.

Mouse Mammary Tumor Virus (MMTV) is a small virus with the classic components and life cycle characteristic of retroviruses. MMTV enters the cells as an RNA copy of the viral genome. In order to replicate and infect, the single-stranded RNA genome must be converted to double-stranded DNA. Several molecules of a virally-encoded RNA-dependent DNA polymerase, reverse transcriptase, and a tRNA primer are encapsulated in the virion to perform this task.

The reverse transcriptase begins synthesizing a DNA copy of the RNA template at a site several hundred base pairs downstream from the 5' end in the U5 region using the tRNA primer. After the direct repeat region (R) has been reverse transcribed, the RNA of the DNA-RNA hybrid at the 5' end is degraded by the RNase H activity of reverse transcriptase enabling the R region at the 3' end to anneal to the newly synthesized DNA. In essence, the reverse transcriptase switches templates and continues DNA synthesis. The RNase H activity of reverse transcriptase also degrades the RNA in the RNA-DNA duplex thus completing the synthesis of a double-stranded DNA copy of the virus. This mode of replication places a short section of the 3' end, U3, at the 5' end and a short section of the 5' end, U5, at the 3' end of the DNA. This structure is identical at both ends of the DNA genome and is directly repeated, U3-R-U5, thus it is termed the long terminal repeat (LTR).

To complete infection, the DNA genome is integrated into the host genome by integrase activity, also a product of the pol gene. Integration occurs at specific sequences in the host genome. A number of these target sequences are located near proto-oncogenes.

The DNA genome can be transcribed and translated producing virions for transmission of the virus. MMTV can be transmitted both horizontally and vertically. Horizontally, transcription of the provirus results in infection of other cells and transmission to offspring through milk. MMTV is transmitted vertically as the provirus through the germ line to next generation.

MMTV is called a latent oncogenic retrovirus because its increased expression is linked to the development of mammary cancers in mice. MMTV's transforming character results from integration of the provirus into or near proto-oncogenes. At least four unrelated genes (int genes) can undergo insertional mutagenesis when integrated; the end result being carcinogenesis (Mink et al. (1990) Nucl. Acids. Res.18:2017–2024).

The MMTV transcription promoter and enhancer region is located in the LTR with the transcriptional start site at 1195 of the 1464 bp LTR-containing fragment as defined by PstI endonuclease digestion. The LTRs are direct repeats of approximately 1.5 kb flanking both the 5' and 3' ends of viral genome, hence two promoters exist. The 5' LTR (left) promoter and enhancer region affect the transcription of the viral genome while the 3' (right) and 5' LTR (left) promoters and enhancers can affect the transcription of genes adjacent to the provirus.

The MMTV LTR contains several regulatory elements which confer steroid inducibility as well as tissue specificity. Of particular interest is the glucocorticoid response element (GRE) located between −204 and −72 relative to the transcriptional start site. The exact location of the GRE domains vary from source to source, but the consensus sequences are contained within this definition of the GRE (Sheidereit et al. (1983) Nature 304:749–752; Mink et al. (1990) Nucl. Acids. Res. 18:2017–2024). The GRE contains four glucocorticoid receptor binding sites as defined by deletion analysis and DNase I protection (Beutti & Kuhnel, (1986) J. Mol. Biol. 190:379–389; Sheidereit et al. (1983) Nature 304:749–752). The consensus sequence for the protein binding domains is 5'-AGAACANNNTGTTCT-3' (SEQ ID NO:1). Either the 5' or the 3' end of the consensus may be homologous to this 15-bp consensus with the right side more highly conserved (Lucas and Granner (1992) Annu. Rev. Biochem 61:1131–73).

As mentioned before, the increased expression of MMTV is linked to the development of mammary cancer in mice. Most infected female mice express increased levels of while pregnant and shed high levels of virus in milk after giving birth (Mink et al. (1990) Nucl. Acids. Res.18:2017–2024). The high levels of expression are due to pregnancy factors, especially the steroid hormone progesterone (Cato et al. (1989) J. Steroid Biochem. 34:139–143. These hormones, progestins, androgens, and glucocorticoids as well as synthetic analogs induce transcription by binding and activating the glucocorticoid receptor which in turn binds to the GRE. This bound protein in turn interacts with other transcription factors such at nuclear factor 1 (NF-1), OTF-1, and perhaps others not yet characterized as inducing transcription (Lucas and Granner (1992) Annu. Rev. Biochem 61:1131–73).

Several variants in the LTR have been discovered and characterized. All of these variants contain deletions and a number of them contain small inserts or repeats. Many of these deletions have been useful in identifying regulatory elements other than the GRE in the LTR.

Hsu et al. (1988) J. Virol. 62:4644–4652, isolated MMTV provirus from C57BL/6 lymphomas and found an identical LTR deletion of 491 base pairs at approximately −655 to −165. The same group found a 430-base-pair deletion in the U3 region of MMTV provirus in BALB/c T-cell lymphomas. In a C3H cell line, MMTV contained a deletion from −637 to −255 which promoted high basal levels of transcription. These findings suggest that the loss of a negative regulatory element contributes to the selective propagation of proviruses with deletions in the LTR.

Using deletion mutations, several regulatory elements have been characterized, including the before-mentioned variants. Two elements have been identified between −631 to −560 and from −428 to −364. The former element, −631 to −560, mediates a negative response in mouse NIH 3T3 fibroblasts, normal mammary gland cells (NMuMG), and also mouse mammary tumor epithelial GR cells. The latter element has negative effects on the NIH 3T3 and NMuMG cells but not the GR cells. Mink et al. conclude that this element could be responsible for cell type specificity.

This same group also identified an orientation element at −1094 to −739. This element has only a slightly higher LTR transcription level, but when placed in the reverse orientation next to a foreign gene, it greatly enhances transcription of that gene. Additionally, this effect was observed in NMuMg and GR cells, but not in NIH 373 cells. This element, therefore, could effect the cell-specific expression of neighboring genes (Mink et al. (1990) *Nucl. Acids. Res.*18:2017–2024).

Recently, another tissue-specific enhancer has been characterized that is apparently independent of lactation. This element, located in the region between −1166 and −987, confers specificity to mammary and salivary gland tissues (MG/SGE for mammary gland/salivary gland enhancer). This enhancer functions in both lactating and non-lactating mammary glands so it appears to be lactation independent. This implies that the MG/SGE acts independently of the GRE. Mok et al. propose that the MG/SGE probably causes MMTV turn on in developing mammary glands while hormonal stimulation during lactation causes the extra high level of MMTV expression needed for infection vertically and horizontally (Mok et al. (1992) *J. Virol.* 66:7529–7532).

Within the LTR, there are two elements that confer tissue specificity, MG/SGE (−1166 to −987) and the GRE (−214 to −72). There are also negative regulatory elements at −631 to −560 and −428 to −364, the latter also exhibiting some cell-type specificity. An orientation dependent-positive element exists at −1094 to −739. This element overlaps the MG/SGE. Except for the GRE, these regulatory elements have been poorly characterized and the cellular factors and their interaction with these elements have not been identified.

XC rat fibroblast tissue culture cells have been used to study MMTV for a number of years. Because MMTV is very tissue and species-specific, there are few tissue culture cell lines that can be infected with MMTV. Because XC cells are large and grow quickly, they are preferable in studies where cell isolates such as RNA are required in larger amounts.

In previous studies, XC rat fibroblast cells infected with MMTV were used to study viral RNA transcription (Robertson and Varmus (1979) *J. Virol.* 30(2):576–589; (1981) *J. Virol.* 40:673–682). The addition of dexamethasone usually results in a 7–20 fold increase in the amount of specific RNA in murine cells infected with MMTV. As part of continuous studies, this cell line was maintained in the presence of $10^{-5}$M dexamethasone for over three years. Over time the fold induction of viral RNA by dexamethasone increased reaching up to 1000-fold. (Robertson and Varmus, (1981) *J. Virol.* 40:673–682). The proviral DNA was isolated from these cells and cloned into a suitable prokaryotic plasmic vector (pTZ18R) for study.

Therefore, in view of the aforementioned deficiencies attendant with prior art methods of expressing high levels of foreign genes in eukaryotic cells, it should be apparent that there still exists a need in the art for eukaryotic expression vectors which are highly inducible and produce low levels of background.

SUMMARY OF THE INVENTION

Accordingly, a major object of the present invention is to provide nucleic acid sequences suitable for use in eukaryotic vectors, which are highly inducible, and yield large amounts of product, including RNA transcripts and proteins.

Another object of the invention is to provide expression vectors for the expression of foreign genes in mammalian cells.

Still another object of the invention is to provide vectors which promote the transcription of DNA sequences into RNA transcripts.

Yet another object of the invention is to provide host cells transformed with these expression vectors.

A still further object of the invention is to provide a method for the expression of foreign genes in mammalian cells.

Briefly, the present invention features an isolated nucleic acid sequence comprising a virally-encoded sequence derived from a region 5' to a transcriptional start site of the virus, wherein the virally-encoded sequences contain at least one direct repeat of a fragment of a hormone-responsive element.

In a preferred embodiment, the virus is a retrovirus, preferably a murine mammary tumor virus.

In another preferred embodiment, the hormone-responsive element is a glucocorticoid responsive element, preferably containing a fusion of the GR1 and GR4 regions.

In other preferred embodiments, the hormone-responsive element is a progestin or mineralocorticoid.

With the foregoing and other objects, advantages and features of the invention that will become hereinafter apparent, the nature of the invention nay be more clearly understood by reference to the following detailed description of the preferred embodiments of the invention and to the appended claims.

BRIEF DESCRIPTION OF THE DRAWINGS

FIG. 8 is a graph of the efficiency of transfecting DNA via electroporation at different voltages. A series of electroporations were performed previously at 50 volt intervals. This graph depicts 20 volt intervals. A sharp peak exists at 320 volts nearly twice as efficient as at 300 volts. All electroporations were done at a capacitance of 500 $\mu F$.

FIG. 10 shows a 78 bp sequence (SEQ ID NO:2) which is repeated two or three times at position −214 in the variant LTRs. The sequence contains two protein binding domains present in the normal LTR, GR1 and GR4, which are indicated beneath the sequence. The concensus sequences, 5'-AGAACANNNTGTTCT-3' (SEQ ID NO:1) are underlined. The italicized sequence at the end of the repeat is also protected from DNase I digestion when bound to the receptor (Scheidereit et al. (1983) Nature 304:749–752).

FIGS. 11A through C shows the sequence alignment of C3H LTR (SEQ ID NO:3) and variant LTRs (SEQ ID NOS:4–8).

FIGS. 17A through I shows the full sequence of the C3H MMTV LTR (SEQ ID NO:9), Variant No.1 LTR (SEQ ID NO:10), Variant No.2 LTR (SEQ ID NO:11), Variant No.3 LTR (SEQ ID NO:12), Variant No.4 LTR (SEQ ID NO:13) and Variant No.5 LTR (SEQ ID NO:14).

DETAILED DESCRIPTION OF THE PREFERRED EMBODIMENTS OF THE INVENTION

Figure 1A:
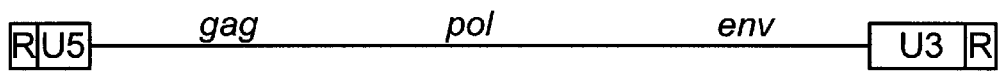
FIG. 1 (Parts A–C) shows the DNA and RNA during the MMTV life cycle. (A) MMTV enters the cell as the single-stranded RNA. By reverse transcription the RNA is converted to double-stranded DNA (B) with long terminal repeats flanking both the ends. (C) Finally, as a product of integration, the target sequences are duplicated at the MMTV-host DNA junction.
Figure 1B:
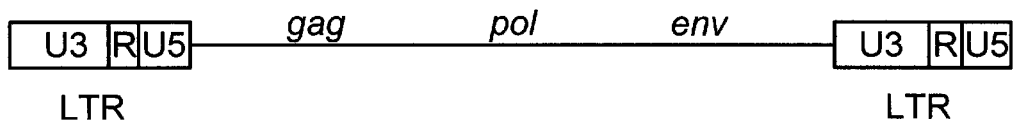
Figure 1C:
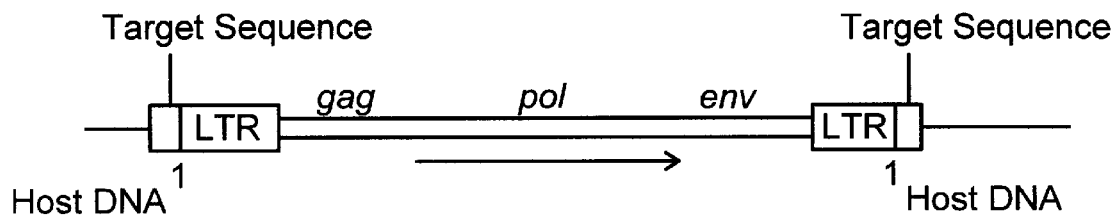
Figure 2:
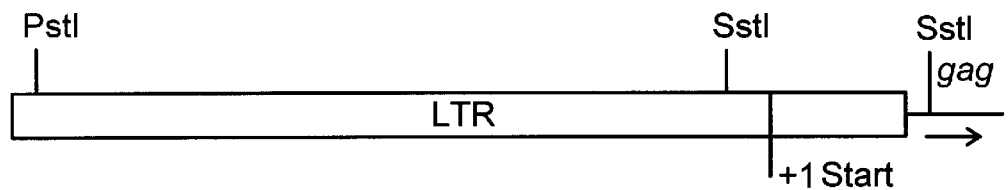
FIG. 2 shows a fragment generated by restriction with PstI restriction endonuclease. The PstI-PstI fragment is 1464 bp in length excluding a small portion of the 5' end of the LTR and including a small fragment at the 3' end. The SstI and transcriptional start sites are also noted.
Figure 3:
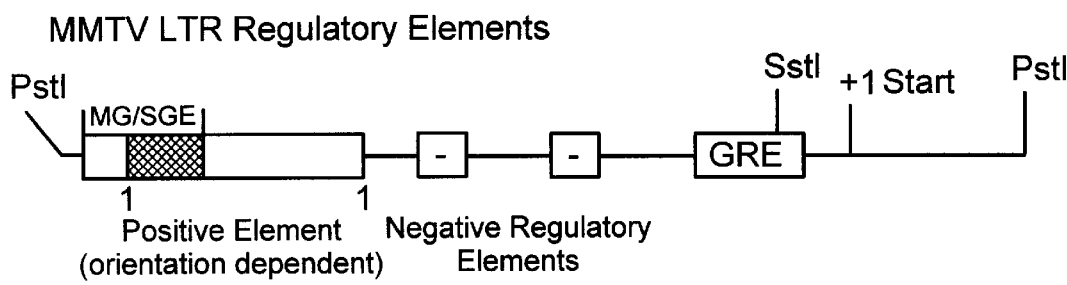
FIG. 3 is a summary of the known regulatory element in the MMTV LTR. MG/SGE is located from −1166 to −987. An orientation-dependent positive regulatory element is located −1094 to −739. The overlap between these two elements is shaded. The two negative regulatory elements are located at −631 to −560 and −428 to −364. Finally, the GRE is located at −204 to −72.

More particularly, the present invention relates to expression vectors containing nucleic acid sequences from a virus in which a hormone-responsive element has been duplicated. The invention also relates to methods of expressing foreign proteins using these vectors.

Expression of foreign proteins in mammalian cells can be used for a variety of purposes, including (1) confirming the identity of a cloned gene; (2) expressing genes encoding proteins which require post-translational modifications; (3) producing large amounts of a protein generally only found in limited quantities; (4) to study the biosynthesis and transport of proteins following expression; (5) to analyze structure-function relationships by analyzing mutant proteins; (6) to express intron-containing sequences which cannot be transcribed correctly in prokaryotes and yeast; and (7) to identify DNA sequence elements involved in controlling gene expression (Sambrook et al, Molecular Cloning: A Laboratory Manual, Cold Spring Harbor Press, Cold Spring Harbor, N.Y., Chapter 16, 1989).

The viral sequences of the present invention can be obtained from any virus in which hormone-responsive size variant elements are observed. However, more preferable are those viruses whose upstream regulatory sequences are active in readily available cells. Moreover, the viral sequences to be used should be active in cells which post-translationally modify proteins in a desired manner. For example, Chinese Hamster Ovary (CHO) cells generally add more terminal sialic acid residues to secretory and transmembrane proteins than do simian CV-1 or mouse NIH-3T3 cells. Id. Moreover, some cells endogenously express high levels of the protein to be expressed, and therefore may not be suitable.

More preferred viral sequences are derived from retrovirus LTRs, and most preferred is murine mammary tumor virus (MMTV). Most preferred among MMTV variants are those variants which contain LTRs which are longer than wild-type, preferably containing extra DNA sequences which are a direct repeat of sequences contained in the glucocorticoid responsive element (GRE).

The viral sequences are preferably obtained from cells infected with the virus. Preferably, the cells have been infected over a substantial period of time, "substantial" meaning more than 6 months, preferably in the presence of the hormone to which the hormone-responsive element responds. The hormone is preferably a steroid hormone, more preferably a glucocorticoid. However, other hormones, including, but not limited to, progestins and mineralocorticoids, are also within the invention.

The virally-encoded sequences can be obtained by isolating total cellular DNA, and digesting with restriction enzymes which cleave either at a known site within a protein-encoding region of the virus, and/or an enzyme which is a rare cutting enzyme, or at least one which is thought not to cleave within the desired viral sequences. Alternatively, the desired virally-encoded sequences may be amplified using polymerase chain reaction (PCR) where appropriate oligonucleotide primer sequences can be determined. The resulting DNA can then be blotted on a Southern blot, or can be directly cloned into an *E. coli*-based vector for selection and propagation.

The virally-encoded sequences can then be analyzed with restriction analysis, using a battery of restriction enzymes which are able to map the restriction sites within the virally-encoded nucleic acid. Alternatively, or additionally, the virally-encoded sequences can be sequenced using known techniques, preferably by the dideoxynucleotide chain termination method of Sanger ((1975) *J. Mol. Biol.* 94:441. Kits such as the Sequenase® system [origin; check trademark] are commercially available for such sequencing.

The sequences obtained can be analyzed for sequence similarity with other known sequences using commercially available software, to locate any hormone-responsive elements, or size variants thereof. Once identified, sequences suspected of being hormonally-induced can be subcloned into an appropriate vector for analyzing induction of transcription under various conditions, including the presence of the hormone of interest. Such vectors include vectors containing a chloramphenicol acetyltransferase (CAT) gene which can be assayed directly in a CAT assay to detect induction of expression. The virally-encoded sequences may also be assayed for protein-binding sequences in a DNA footprinting assay.

Virally-encoded sequences of the present invention are preferably those which are a direct repeat of a fragment of 20–200 bp in length, more preferably about 50–100 bp in length, and most preferably about 75–80 bp in length. In particular, extra sequences which are direct repeats of a 78 bp fragment containing the DNA derived from nucleotides −214 to −156 (GR1) fused to the DNA located between nucleotides −91 to −72 (GR4) are most preferred. The variant LTRs may contain at least two copies of this GR1/GR4 fusion, and also preferably contain the normal GRE downstream from the GR1/GR4 fusion repeats. Expression of foreign genes using these variant LTRs can be induced more than 100 fold with dexamethasone.

The virally-encoded sequences of the present invention are also useful for directing transcription of DNA sequences into RNA transcripts. Preferred embodiments include sequences which direct the transcription of DNA sequences into antisense RNA and other structural and functional RNAs.

The cells which are chosen for as hosts for the expression vector of the present invention may either transiently express the foreign DNA, or may be stably transfected such that they express the foreign DNA constitutively. Whether the cells are transient or stable expressors depends on the nature of the cells and virally-encoded sequences. Cells and cell lines in which such virally-encoded sequences are active are well known in the art, and include COS cells, CV-1 cells and a broad range of mammalian cells for SV40-derived sequences, murine C127 cells for BPV-derived sequences, and a broad range of host cells for Epstein-Barr derived sequences. In general, host cells will preferably be from the species in which the virus naturally occurs.

The expression vectors of the present invention must contain various control elements necessary for the expression of the foreign gene. In particular, the vectors must contain a promoter, ribosome binding site and polyadenylation sequences, and preferably also enhancers, and splice acceptor and donor sequences.

The promoter preferably contains a TATA box, about 25–30 bp upstream from the transcription initiation site, and also preferably contains upstream promoter elements about 100–200 bp upstream of the TATA box, which determine the rate at which transcription is initiated. Enhancers such as that derived from SV40 virus, may be active in a wide range of host cells. The U3 region of LTRs generally contain all of these sequence elements.

The plasmid should also contain termination sequences which are generally a few hundred nucleotides in length, and downstream from the polyadenylation site. A polyadenylation signal is comprised of GU- or U-rich sequences located downstream from the polyadenylation site and a conserved sequence, AAUAAA, located 11–30 nucleotides upstream. A preferred polyadenylation signal is obtained from a 237 bp BamHI-BclI SV40 restriction fragment. The U3 region of the LTR generally contains such sequences. The plasmid should also be devoid of sequences known to destabilize mRNA (Shaw and Kamen (1986) *Cell* 46:659.

Consensus splice sites for removing introns from the mature mRNA preferably contain the following sequences (SEQ ID NO:15):

5' AG:GU(A)AGU . . . intron . . . (U/C)$N_{11}$CAG:G 3'.

The plasmid should also contain a consensus sequence (SEQ ID NO:16) for initiation of translation by eukaryotic ribosomes, preferably:;

GCCGCCA$^{-3}$/GCCA$^{1}$UGG$^{+4}$.

Other vectors included within the invention are those which are used to direct transcription of DNA sequences into RNA transcripts. Preferred vectors direct the transcription of DNA sequences into antisense RNA and other structural and functional RNAs.

In order for the plasmid to be constructed and propagated in bacteria, the plasmid should preferably contain a replicon which functions in *E. coli*, a gene encoding antibiotic resistance, and specific limited restriction sites. The bacterial sequences may be derived from the bacterial plasmid pBR322. The plasmid should also be devoid of sequences known to interfere with eukaryotic expression (Lusky and Botchan (1981) *Nature* 293:79.

The vector should also contain a selectable marker for selecting transfected cells. Such selectable markers include thymidine kinase (transfected cells grown in 5-bromodeoxyuridine), dihydrofolate reductase (transfected cells grow in the absence of thymidine, glycine and purines), aminoglycoside phosphotransferase (transfected cells grow in the presence of kanamycin, neomycin and geneticin), hygromycin B phosphotransferase (transfected cells grow in the presence of hygromycin), xanthine-guanine phosphoribosyl transferase (transfected cells lacking HGPRT grow in HAT medium, wild type transfected cells grow in medium containing adenine, xanthine and mycophenolic acid), CAD (carbamyl phosphate synthetase, aspartate transcarbamylase and dihydroorotase; transfected cells lacking CAD grow in the absence of uridine), adenosine deaminase (transfected cells grow in high concentrations of adenosine), and asparagine synthetase (transfected cells grow in asparagine-free medium containing the glutamine analog albizziin).

Optionally, the plasmid may contain transforming sequences which allow for the establishment of stably transfected cell lines. An example is the 69% transforming fragment from bovine papillomavirus (BPV).

The plasmids may be introduced into the host cells by any means known in the art, including transfection using calcium phosphate, DEAE-dextran, lipofection, polybrene, by protoplast fusion, electroporation, liposome or direct microinjection into the nucleus of the host cell.

In a preferred embodiment of the invention, an XC rat fibroblast cell line infected with mouse mammary tumor virus (MMTV) was grown in the presence of dexamethasone for over three years. The amount of viral RNA in these cells was significantly increased compared to the original MMTV infected cells. Proviral LTRs from these cells were larger than normal with extra DNA sequences of between 154 and 232 base pairs inserted at position −214 relative to the +1 transcriptional start of MMTV.

These modified LTRs were sequenced and compared to the normal LTR. The extra sequences are direct repeats of a 78 bp fragment containing the DNA derived from nucleotides −214 to −156 (GR1) fused to the DNA located between nucleotides −91 to −72 (GR4) of the wild type LTR. These alterations resulted in a fusion of GR1 to GR4 so that the variant LTRs contain either two or three copies of this 78 bp GR1/GR4 fusion. Downstream from these insertions, the normal GRE, consisting of domains GR1, GR2, GR3, and GR4 is also present in all variants except one. In this variant the normal GRE has been completely eliminated and replaced by three copies of the 78 bp GR1/GR4 fusion sequences.

These LTR variants attached to the chloramphenicol acetyltransferase (CAT) gene were used to monitor the extent of induction by dexamethasone for each modified LTR compared to the normal MMTV LTR. These studies revealed that the addition of dexamethasone increased the CAT activity 75 to 165-fold over no dexamethasone depending on the variant.

From the evidence available, the high inducibility of the variant LTRs is due to the 78 bp repeats inserted immediately upstream from the normal GRE. Because these repeats contain glucocorticoid receptor (GR) binding domains, the multiple binding of GR is likely to be responsible for the high level of transcription. However, there are other factors necessary to induce transcription on the hormone response unit (HRU—the GRE, NF-1 and OTF-1 binding domains) of MMTV other than the GRE (Lucas and Granner (1992) Annu. Rev. Biochem. 61:1131–73). Deletion of the NF-1 binding site renders the GRE- non-responsive to glucocorticoids but not progesterone. If the distal OTF-1 site is also deleted, the progesterone responsiveness is drastically reduced. The binding of NF-1, OTF-1, and/or other factors are necessary in addition to the binding of GR's at the GRE.

Figure 16:
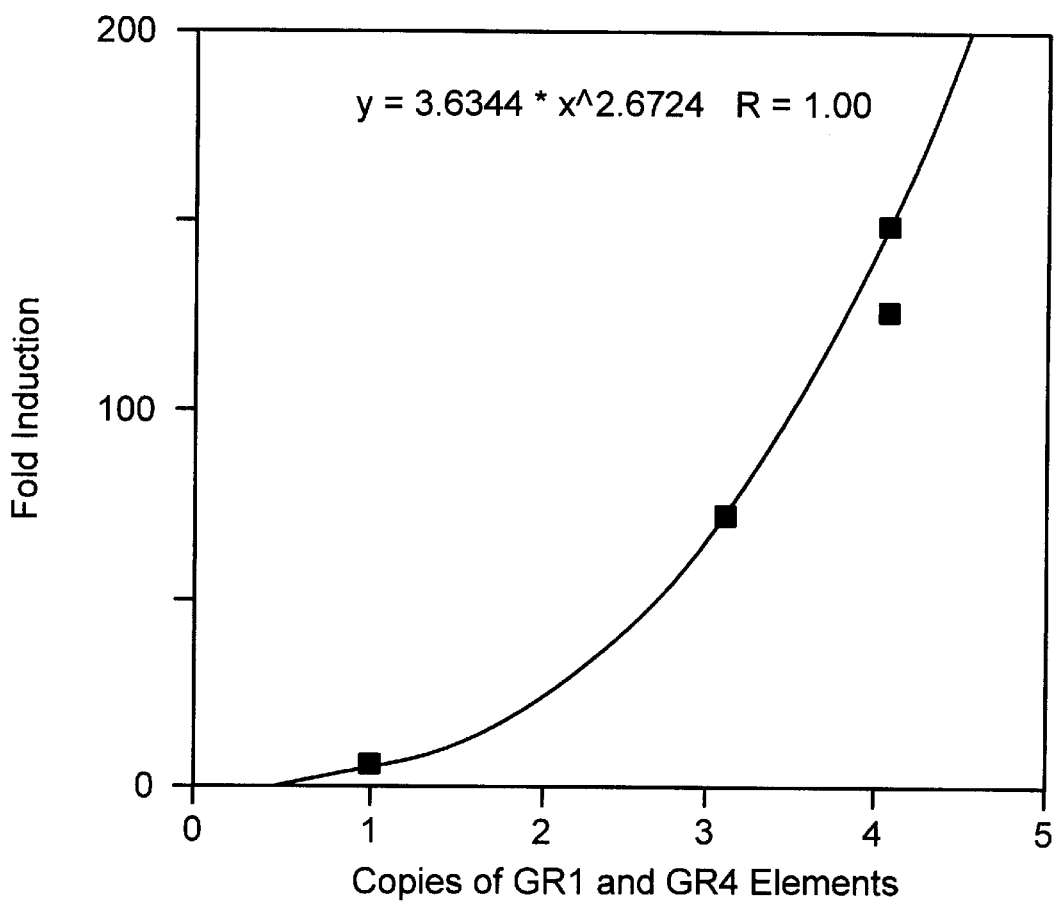
FIG. 16 is a plot of the fold-induction versus the number of GR1/GR4 elements. The curve has been fit with a logarithmic equation. Notice that R=1.00 so the curve fits nicely. Also the data point at 3 is really two data points.

The fold-induction of the LTR variants increases in a non-linear fashion relative to the number of GR1 and GR4 elements. FIG. 16 shows the relationship between the number of response elements versus fold-induction with a curve fit. The curve through these five points appears to be logarithmic.

The wild-type MMTV LTR has previously been used for the regulated expression of foreign genes in eukaryotic cells. The variant LTRs of the present invention respond 20 to 50 times stronger to dexamethasone than does the wild-type GRE and yet background from both LTR's is virtually the same. The application of 165-fold induction in a eukaryotic system makes the variant LTRs of the present invention even more useful for the expression of high levels of foreign proteins in eukaryotic cells.

The following examples are presented in order to more fully illustrate the preferred embodiments of the invention. They should in no way be construed, however, as limiting the broad scope of the invention.

EXAMPLE 1
MMTV LTR variants

LTR variants were previously isolated from infected XC rat fibroblast tissue culture cells and cloned into *E. coli* plasmid pTZ18R for maintenance, sequencing, and characterization.

EXAMPLE 2
Restriction Mapping

Figure 4:
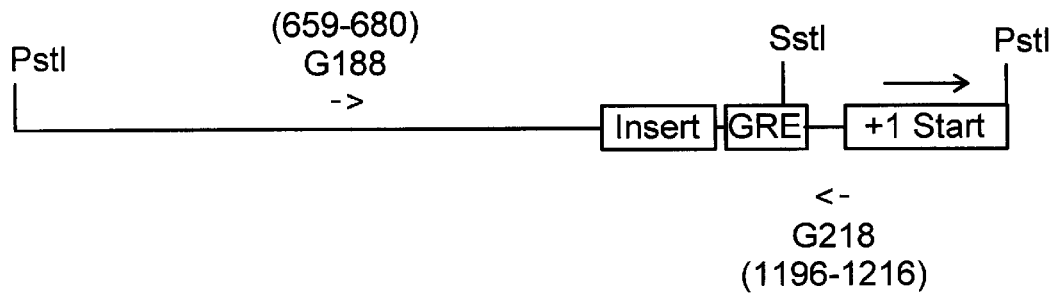
FIG. 4 is a map of the MMTV LTR used in all experiments. The insert at −214 varies in size depending on the number of repeats. G188 and G218, the primers used in sequencing and amplifying the short fragment, are shown with an arrow to indicate position and orientation. The PstI, SstI, and transcriptional start site are shown for orientation.

LTR variants were restricted with several enzymes to determine the location of the variation. The variation mapped near the SstI restriction site (FIG. 4). At this level the size of the insert was indiscernible, but LTR variants fell into several size categories.

EXAMPLE 3
Sequencing

Two or three different samples of similar size were selected for Sanger Dideoxynucleotide sequencing. Sequencing reactions were carried out as described by United States Biochemical (USB, 1990). Samples were electrophoresed on a 6% denaturing polyacrylamide gel and used to expose Kodak X OMAT X-Ray film overnight. Primers G218 and G188 were chosen to sequence the region containing the SstI restriction site (FIG. 4). Sequences were recorded using the Beckman Gelmate™ 1000 Sonic Digitizing System and stored and analyzed using MicroGenie™ also from Beckman. All analyses of sequences were done using MicroGenie™.

Figure 9A:
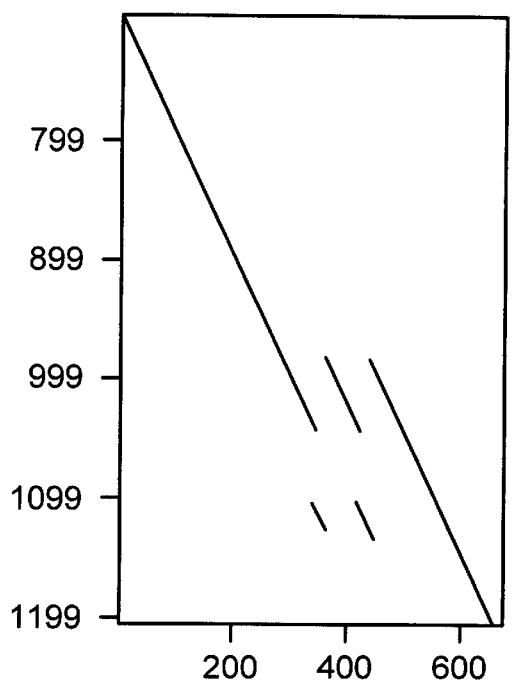
FIG. 9 is a matrix comparison of three variant LTRs with the wild-type C3H MMTV LTR. A dot corresponds to homologous base pairs in sequence. Perfect homology would be indicated by a straight line. The first variant LTR (gre1) contains two duplicated GR1/GR4 domains, in addition to the normal GRE. The second variant LTR (gre2) contains three duplicated GR1/GR4 domains, with a GRE which lacks domains GR2 and GR3 (see FIG. 11 for position of deleted nucleotides in variant #2 immediately preceding nucleotide number 435). The third variant LTR (gre5) contains three duplicated GR1/GR4 domains, in addition to the normal GRE.
Figure 9B:
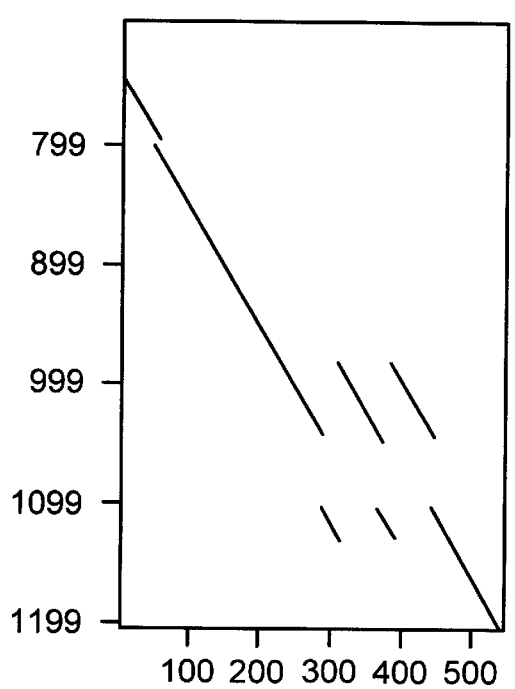
Figure 9C:
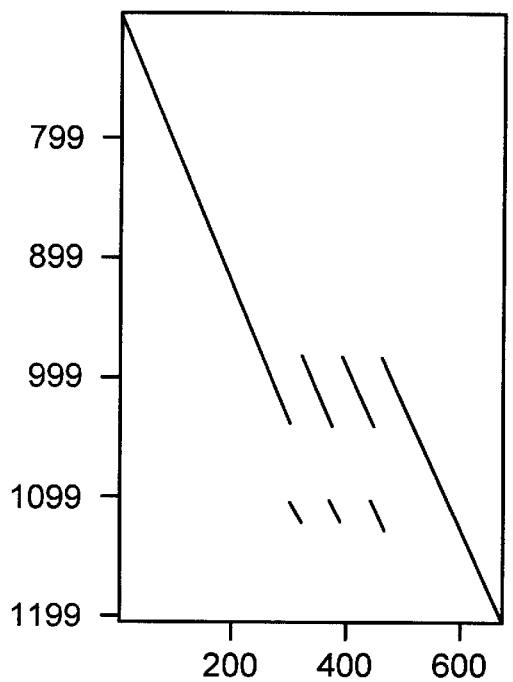
Figure 12A:
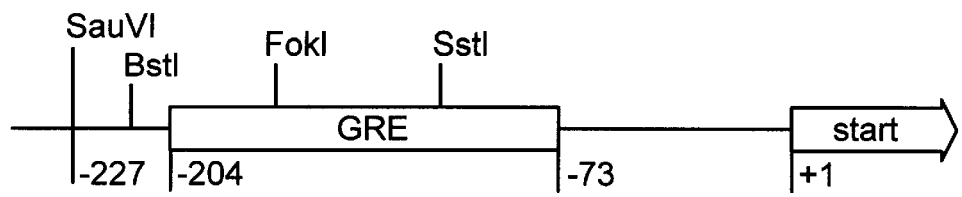
FIG. 12 (Parts A–D) shows constructs of the LTRs, wild-type and variant, showing the location and frequency GR1/GR4 fusion and normal GRE. Restriction sites are indicated for orientation and the transcriptional start is represented with a large arrow. (A) represents the structure of the normal wild-type LTR; (B) variants #1 and #3; (C) variants #4 and #5; and (D) variant #2. (B) contains two repeats while (C) has three. Variant #2 is missing the normal GRE completely.
Figure 12B:
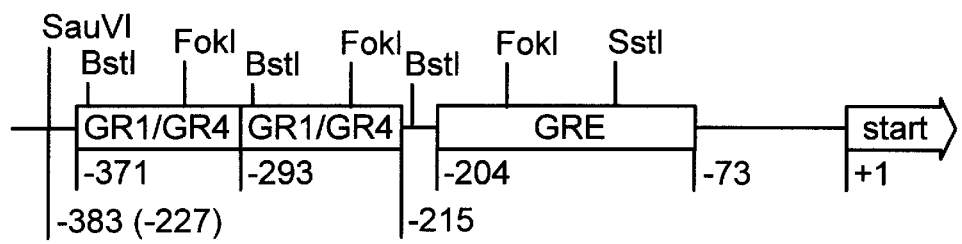
Figure 12C:
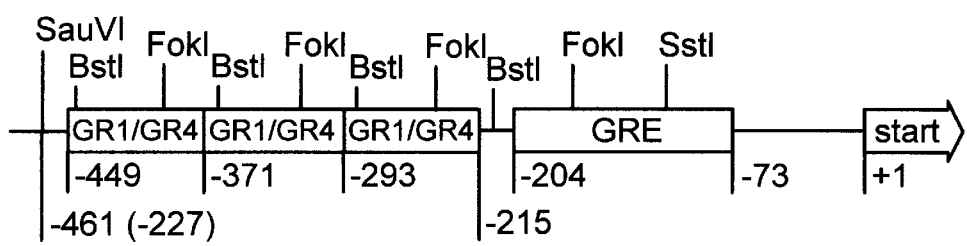
Figure 12D:
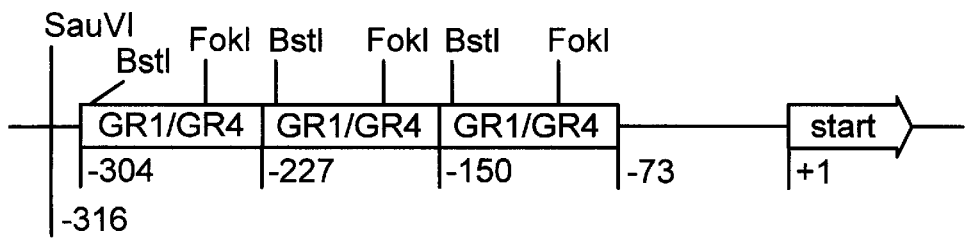

Matrix comparison of the variant MMTV LTRs with the wild type (C3H) maps the abnormalities between base pairs 980 and 1130 of the LTR corresponding to −214 and −72 relative to the MMTV LTR transcriptional start site. Two samples of each size were analyzed and each matrix comparison showed similarities (FIG. 9). Homology sequence analysis revealed that the repeated regions in each variant were 78 bp and in one case 79 bp repeats inserted immediately upstream from the normal GRE (roughly −204 to −72). The 78 bp repeat contains two of the glucocorticoid receptor binding domains defined as GR1 and GR4 in the wild type GRE (FIG. 10). The result of this repeat is a GR1/GR4 fusion product inserted upstream from the start site and normal GRE. Two or three copies of this GR1/GR4 repeat are present in each variant LTR, and in one case, variant #2, the wild type GRE is completely missing. The sequences of the variant LTRs and the wild-type C3H LTR were aligned to identify disparities (FIG. 11). FIG. 12 illustrates the structure of each variant LTR in the GRE region. Variants #4 and #5 are identical and variants #1 and #3 are nearly identical. Variant #2 is unique in that it contains no normal GRE. Therefore a fragment −155 to −92, which is present once in all other LTRs (variants and wild-type) is not present in variant #2.

The sequence of the pCAT-LTR construct of variant #3 (SEQ ID NO:12) revealed a deletion in the 5' region of the LTR downstream from the transcriptional start. A purine mutation from G to A at +129 relative to the transcriptional start site changed the sequence from 5'-CTGCGG-3' to 5'-CTGCAG-3', a PstI restriction site. Cleavage at this new site truncated the fragment cloned into the CAT vector and the resulting construct puts the MMTV transcriptional start 139 bases closer to the AUG start of the CAT gene.

EXAMPLE 4
Preparation of pCAT®-BASIC—LTR Variant Constructs
Cloning the LTR

Figure 5:
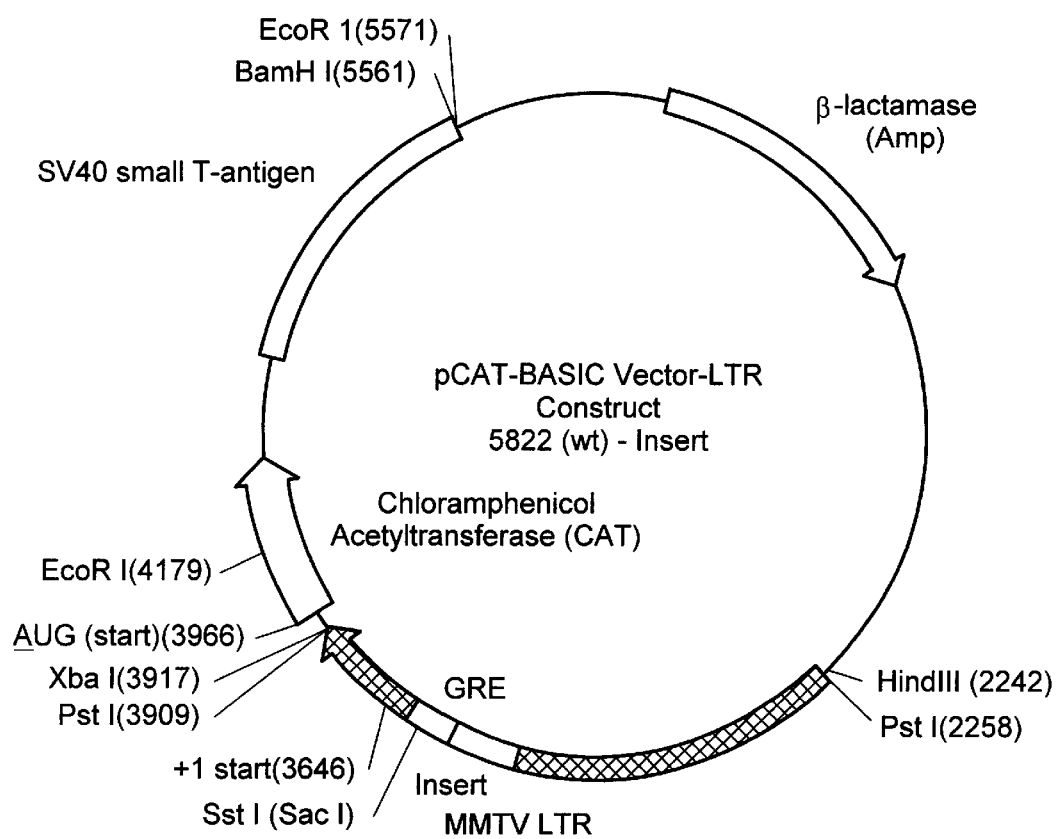
FIG. 5 is a map of the pCAT®-Basic (Promega, Madison, Wis.) expression vector with the MMTV LTR in the proper orientation to promote transcription of the chloramphenicol acetyltransferase gene. The transcriptional and translation start sites as well as notable restriction sites are shown. The size of the plasmid with the normal LTR is 5822 bases. The size of the plasmid with a variant LTR is 156 to 234 bp larger.

To characterize the induction and hormone response of the variants, the entire LTR between the Pst I sites was cloned into pCAT®-Basic vector (FIG. 5) produced by Promega Corporation. Again, two variants of each size were cloned. Three methods were used to clone the LTR into the pCAT®-Basic vector each of which will be described briefly.

1. Restriction-Ligation. The expression vector and the mother plasmid, pTZ18R were each restricted with Pst I restriction endonuclease. The expression vector was then treated with shrimp alkaline phosphatase (SAP) as described by manufacturer to reduce self ligation (United States Biochemical, Cleveland, Ohio). Both DNAs were ethanol/ NaAc (95% ethanol with ½oth volume 3.0M NaAcetate at pH 5.2) precipitated in the same microfuge tube. Ligation was done with T4 DNA ligase under conditions described by the manufacturer (USB, Cleveland, Ohio). The ligation reaction product was used to transfect E. coli XL1-Blue bacteria as described below under "electroporation".

2. LTR Isolation-Ligation. The expression vector and mother plasmid containing the LTR were restricted and treated as in "1" above but the pTZ18R-LTR reaction was electrophoresed on a 0.8% agarose gel containing 1X TAE (40 mM Tris-Acetate, 1 mM EDTA). The DNA was stained with ethidium bromide and visualized under UV light. The LTR band was cut directly from the gel with a razor blade and then expressed through a sterile syringe to disrupt the agarose. The DNA was then recovered from the agarose by one equilibrated phenol extraction, followed by one phenol:chloroform (1:0.5) extraction and ethanol/NaAc precipitation. The restricted expression vector and LTR fragment were combined and ligated as described in "1" and then electroporated.

3. PCR Amplification-Ligation. The variant LTR's within pTZ18R were amplified via PCR using the M13 universal and reverse primers. PCR was carried out as described by Promega, the source of the Taq DNA polymerase. The PCR cycles were as follows:

1× 94° C. for 4:00 min.
30× 94° C. for 0:15
   45° C. for 0:15
   72° C. for 2:00
1× 72° C. for 4:00

The PCR product was then electrophoresed on a 0.8% agarose gel to confirm the amplification. PCR products and the expression vector were then restricted with PstI and ligated as described in "1" above and then electroporated as described below.

EXAMPLE 5
Electroporation

From the ligation reaction mixture, 1 µL was combined with 40 µL electrocompetent E. coli XL1-Blue cells and transferred to a 0.2 cm gap electroporation cuvette. (1 µL or less of ligation mixture was used regardless of DNA concentration to keep salt concentrations and conductivity low to prevent arcing during the electroporation pulse.) Electrocompetent E. coli XL1-Blue cells were prepared as described by BioRad and electroporated at suggested voltage, capacitance and parallel resistance on the Bio-Rad Gene Pulser™ equipped with a Pulse Controller™ (Bio-Rad1, pp. 16–17). The time constant for each electroporation pulse reaction was either 4.4 or 4.3 msec. As suggested, cells were suspended in 1 mL SOC media immediately after pulsing and incubated for 1 hour at 37° C. to allow expression of antibiotic resistance. Cells were then plated on LB-agar plates containing ampicillin (100 µg/mL) and incubated overnight.

EXAMPLE 6
Selection and Detection of LTR-Vector recombinants

Three methods were used to detect recombinant plasmids, quick screen, radioactive probe, and PCR screen. The only sure way of detecting properly recombined plasmid was to screen for the LTR in the pCAT vector directly because both the mother and expression plasmids were ampicillin resistant and the pCAT vector provides no other means of selection.

1. Quick screen. Plates containing possible recombinant colonies were picked and combined with 1–2 mL Luria Broth (L-Broth) and grown overnight in shaking incubator at 37° C. About 1 mL of the overnight culture was added to a microfuge tube and centrifuged for 1 minute. The cell pellet was resuspended in 100 µL hi TE (250 mM Tris, 100 mM EDTA) and extracted once with an equal volume of phenol:chloroform (1:0.5). The aqueous phase was combined with loading buffer and electrophoresed on a 0.8% agarose gel with the running buffer not overlaying the gel until after the sample had entered the gel. The gel was then stained with ethidium bromide, and visualized under UV light. Possible positives were selected by size relative to supercoiled plasmid standards.

Figure 6:
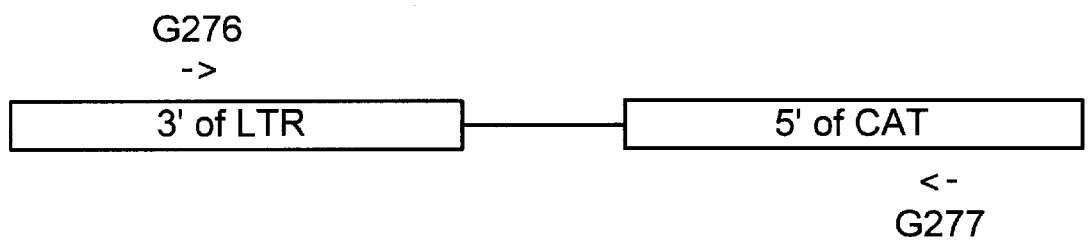
FIG. 6 is a schematic presentation of the junction between the expression vector containing the CAT gene and the MMTV LTR. In the proper orientation the junction will include the 3' end of the LTR. G276 and G277 are oligonucleotides 22 bp in length used in PCR to amplify the fragment spanning this junction. PCR on colonies which yields a fragment about 0.55 kb in length indicates that the LTR is in the expression vector in the proper orientation.

2. PCR screen. The anticipated sequence of the variant LTR's in the expression vector in the right orientation was entered into the primer selection program called Primer Detective™. Two primers, one in the LTR (G276) and the other in the CAT gene (G277) were selected (FIG. 6) to specifically amplify a small fragment within the recombinant expression plasmid containing a variant LTR in the right orientation. PCR was performed directly on colonies from electroporation. One-fifth the normal volume of a PCR reaction, 10 µL was prepared and a toothpick picking of a colony was applied directly to the reaction. A picking of the identical colonies was combined with 2 mL L-Broth in test tubes and grown overnight to preserve colonies for later retrieval. PCR was cycled as follows:

PCR Cycles
1× 94° C. for 4:00 min.
25× 94° C. for 0:15
   60° C. for 0:15
   72° C. for 1:00
1× 72° C. for 4:00

The PCR product was electrophoresed directly on a 0.8% agarose gel, stained with ethidium bromide, and visualized under UV light. The presence of a 0.5 kb band indicated a positive recombinant expression vector and also the correct orientation.

3. Radioactive Probe. Colonies from the electroporation of the ligation mixture were gridded on ampicillin-containing plates for easy identification and isolation. A radioactive probe was made by Klenow fragment elongation of CT-primers using the gel-isolated LTRs as a template with α-labeled $^{32}$P-dATP. Colonies on gridded plates were lifted off with a nylon hybridization transfer membrane and allowed to dry. Filters were treated with 1× denaturing buffer (0.5M NaOH, 1.5M NaCl) for 10 minutes and then denatured with Tris/NaCl (140 mM Tris-HCl, 1.5M NaCl) twice for 5 min. Finally filters were washed with 10× SSPE (1.5M NaCl, 0.1M NaH$_2$PO$_4$ pH 7.4, 10 mM EDTA) and air dried. Filters were prehybridized at 650° C. for 2 hours in a hybridization bottle in the Robbins Scientific Hybridization Incubator. One million counts of probe were added per filter and hybridized overnight. The following day, filters were washed three times for 15 minutes at 53° C. in 0.1% SDS (sodium dodecylsulfate) and 1× SSPE (0.15M NaCl, 10 mM NaH$_2$PO$_4$ pH 7.4, 1 mM EDTA). Dried filters were fixed to 3 MM paper with removable tape and exposed to X-ray film in a cartridge with intensifying screens at −70° C. for 14–18 hours. Positive colonies appear as intense black circles on the developed X-ray.

EXAMPLE 7
Restriction Analysis of Constructs

Only the PCR amplification-ligation method of cloning was successful and colonies were detected by all three screening procedures. Colonies containing positive recombinant expression plasmids were grown up large scale and these DNAs were used for restriction analysis. Constructs were restricted with SstI and HindIII restriction endonucleases to confirm the proper orientation of the LTR in the expression vectors (see FIG. 5). A larger 4.4 kb fragment and smaller fragments from 1.1 to 1.4 kb indicated the proper orientation. If the larger fragment was variable in size, it would indicate the opposite orientation.

Additionally, pCAT®-BASIC-LTR variant constructs were sequenced from primer G277 (refer to FIG. 6) to double-check success in cloning the LTR into the expression vector in the correct orientation. Sequence analysis revealed a mutation in the 3' end of one LTR that resulted in an additional PstI restriction site. Consequently, a truncated LTR was cloned into the expression plasmid with the end result being a deletion between the transcriptional start site and the AUG start of the CAT gone of 139 base pairs.

EXAMPLE 8
Electrotransfection of pCAT®-BASIC-LTR Variant Constructs

Tissue Culture Cell Preparation

XC rat fibroblast tissue culture cells were maintained on Dulbecco's Modified Eagle's Medium fortified with 10% fetal calf serum and treated with gentamicin, a broad range antibiotic (DMEM-FCS). At 75% to total confluency the cells were prepared by first one rinse with Puck's EDTA followed by treatment with trypsin containing solution to release cells (STV-Puck's EDTA with trypsin). Once cells were loose from plates, the cells were collected in a 50 mL conical plastic centrifuge tube, combined with an equal volume of DMEM-FCS and centrifuged for five minutes at 1750 RPM (¾ speed) in a clinical centrifuge. Cells were resuspended in ice cold Dulbecco's Phosphate Buffered Saline with no Mg$^{2+}$ or Ca$^{2+}$ (hereafter referred to as simply PES) and centrifuged as before. Cells were finally resuspended in a volume of PBS sufficient to use 0.8 mL cells for each variant LTR electroporation reaction. This volume was usually 6.5 mL, enough for eight reactions (BioRad Gene Pulser transfection apparatus operating instructions and application Guide).

EXAMPLE 9
PEG precipitation of DNA

Highly pure DNA is required for transfection experiments. Commonly, CsCl centrifugation is used to purify the DNA. Instead we used a new polyethylene glycol (PEG) precipitation procedure reported in Biotechniques. The PEG solution (40% PEG, 30 mM MgCl$_2$) was prepared as described by Nicoletti and Condorelli (1993). pCAT®-BASIC-LTR Variant Constructs in *E. coli* XL1-blue cells were grown overnight on Terrific Broth (Applied Biosystem User Bulletin 18, 1991). DNA was then purified as described by Nicoletti and Condorelli ((1993) *BioTechniques* 14(4) :532–536). The absorbance of these purified DNA solutions was measured at 260 nm and an equal volume of each sample was electrophoresed on an 0.8% agarose gel. After staining with ethidium bromide, the intensity of fluorescence due to the UV illumination was noted and compared to the concentration calculated from the spectrophotometric analysis. The staining intensity corresponded well with the spectral readings indicating that the concentration calculated from absorbance at 260 nm was accurate.

EXAMPLE 10
Electroporation of Tissue Culture Cells

Figure 7A:
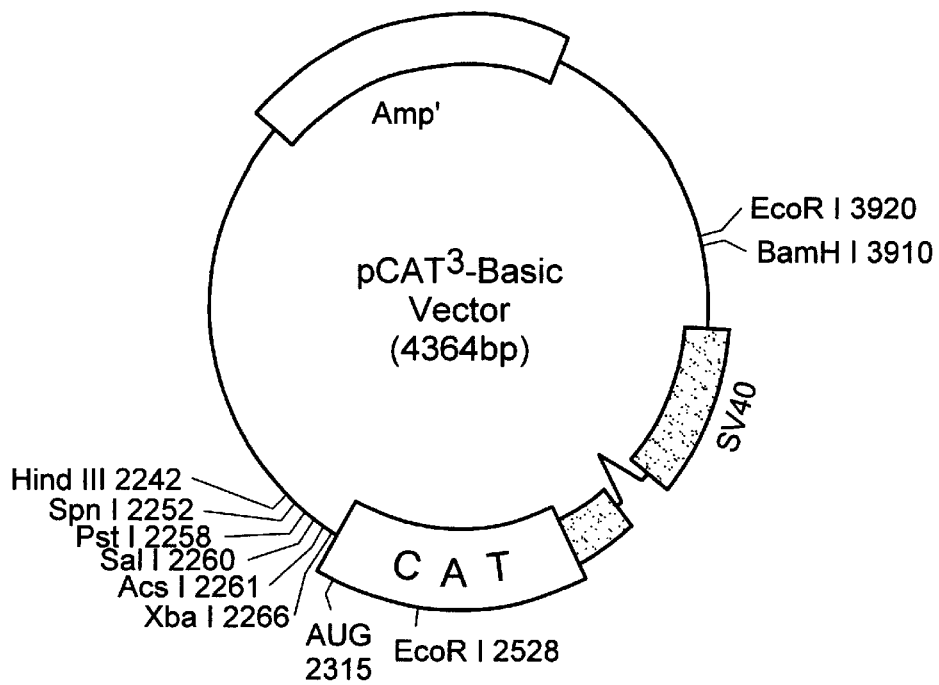
FIG. 7 gives descriptions of the expression vectors used for CAT assays. The Basic vector (above) was depicted with an insert in FIG. 5. The Control vector was used as a positive control and to optimize electrotransfection conditions. The Basic vector contains no promoter or enhancer sequences while the Control vector has the SV40 early promoter and SV40 enhancer.
Figure 7B:
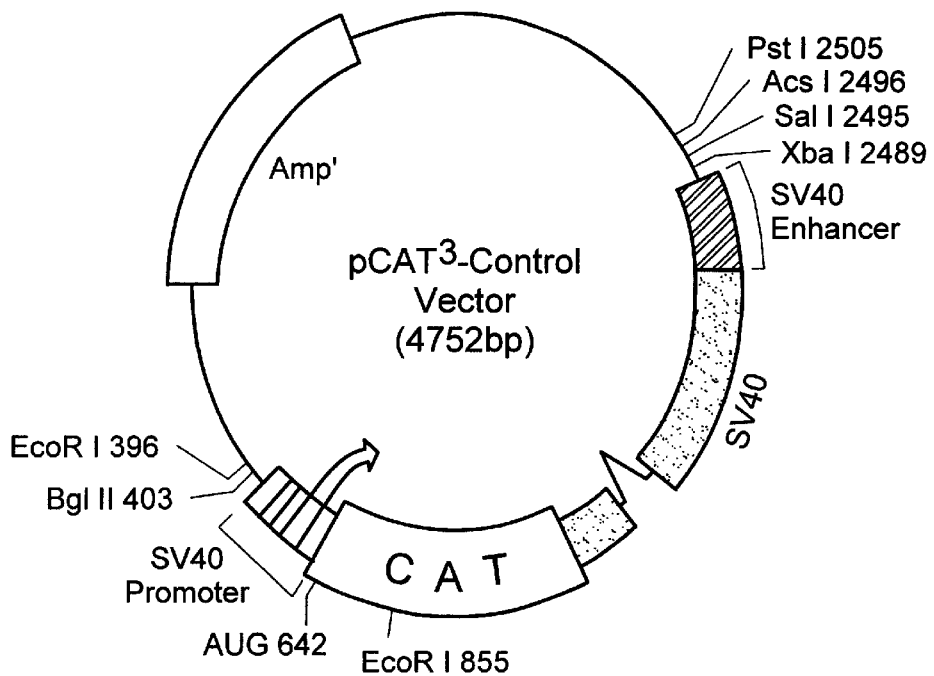

To find the optimum transfection efficiency conditions, a series of voltages and capacitances on the BioRad Gene Pulser® were used guided by experiments done previously (Chu et al., (1987) *Nucl. Acids Res.* 15(3):1311–1325; Bio-Rad2). Efficiency was measured by chloramphenicol acetyltransferase activity produced from transcription and translation of the pCAT®CONTROL VECTOR from Promega Corp. which contains the SV40 early promoter and enhancer sequences (Promega Technical Bulletin 081, 1991) (FIG. 7). With 50 Volt intervals, a maximum efficiency was found at 300 Volts and 500 μF capacitance. These conditions were used for electroporation experiments. The time constant for this pulse was between 5.9 and 6.3 milliseconds depending on the concentration of the cells and the volume of the DNA aliquot which contained Tris. When the volt intervals were decreased to 20 Volts, 320 Volts and 500 μF were found closer to the optimum (FIG. 8).

Electroporation reactions contained 0.8 mL XC rat fibroblast tissue culture cells in PBS (no Mg$^{2+}$ or Ca$^{2+}$) and 20 μg expression plasmid. Reactions were pulsed at room temperature and let stand for approximately 10 minutes at the same temperature. Each reaction was then split equally and plated on two 60 mm sterile tissue culture dishes; one containing 3 mL DMEM-FCS and one containing 3 mL DMEM-FCS with 10$^{-5}$M dexamethasone. Cells were allowed to grow 48–72 hours before harvesting.

EXAMPLE 11
CAT Assay

Transfected cells were harvested as described by Promega Corporation using the Reporter Lysis buffer method (Promega Technical Bulletin #084, 1991). Cell extracts were either assayed for CAT activity directly or frozen at −70° C. and assayed later. CAT activity from frozen cell extract vs. cell extract used immediately was not significantly different. Also, the fold induction as revealed by the assay remained constant for frozen and fresh cell extract.

The method for assaying the cell extract was modified slightly because of the high production of the protein in the presence of dexamethasone. Chloramphenicol [Ring-3,5-$^3$H] (NEN Cat. #NET-928) at 32 Ci/mmol was first diluted 1560-fold with chloramphenicol in ethanol giving a final stock specific activity of 32 mCi/mmol. Immediately before each assay, this stock was diluted 10-fold in 0.25M Tris-HCl, pH 8.0 and 10 μL of this diluted solution was used for a 125 μL assay reaction giving a final concentration of 51.2 μM chloramphenicol (⅟$_{1000}$th $^3$H-chloramphenicol).

To assay the variants, 110 μL of each cell extract was combined with 5 μL n-butyryl coenzyme A (5 mg/ml) and 10 μL of diluted chloramphenicol stock resulting in a final volume of 125 μL. As a negative control, cell extract was replaced with pure 1× reporter lysis buffer (Promega) and as a positive control a series of 0.5, 0.025, 0.0125 and 0.00625 units of chloramphenicol acetyltransferase supplied by Promega (Cat. #E1051) was added with distilled water to a volume of 125 µL. As an additional negative control, cell extract from non-transfected XC cells was also assayed for CAT activity. The assay reaction was incubated at 37° C. for 2, 3, 4, 6 or 20 hours depending on the level of protein production. Extracts from the same transfection reaction were kept under identical conditions for identical time periods.

After incubation 300 µL of mixed xylenes were added as described in Promega Technical Bulletin #084 (1991). After back extractions 250 µL of xylenes were added to 5 mL of Bio-Safe II* scintillation cocktail produced by Research Products International Corp. in 20 mL glass capped scintillation vials and shaken vigorously to mix. Samples were counted in the Minaxi Tri-Carb 4000 Series scintillation counter from United Technologies Packard.

Figure 13A:
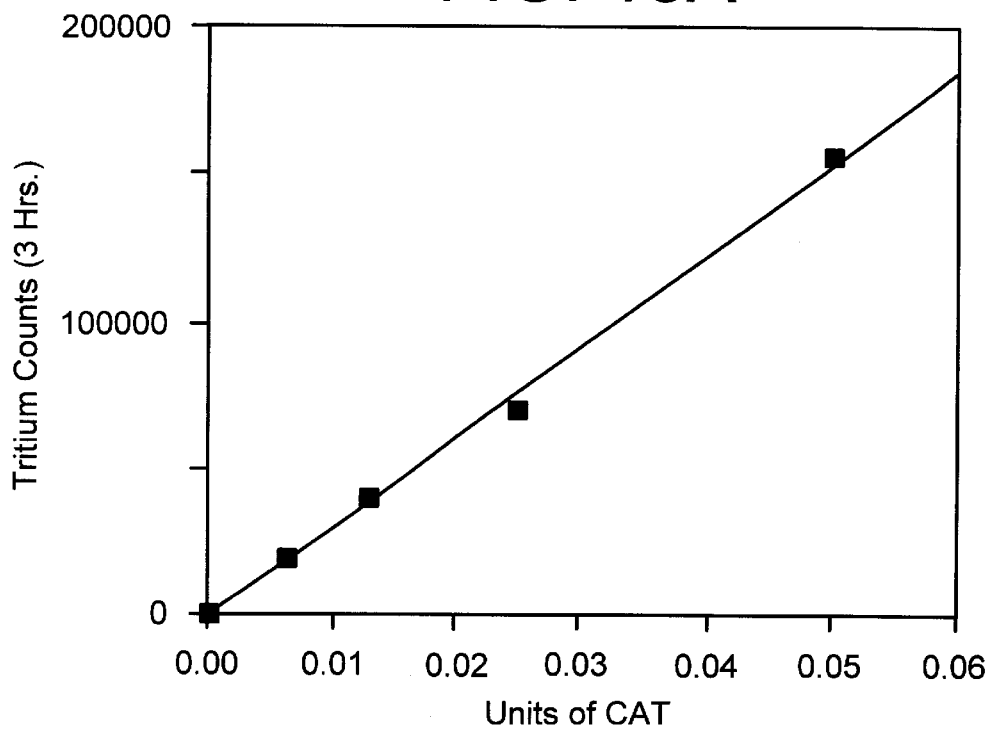
FIG. 13. The top graph represents CAT activity relatively unlimited for three hours. The activity is linear with the amount of enzyme. The lower graph shows the enzyme as it becomes substrate limiting. All data were obtained from three hour assays on differing amounts of enzyme. Counts much over 350,000 CPM indicate the reaction has become substrate limiting.
Figure 13B:
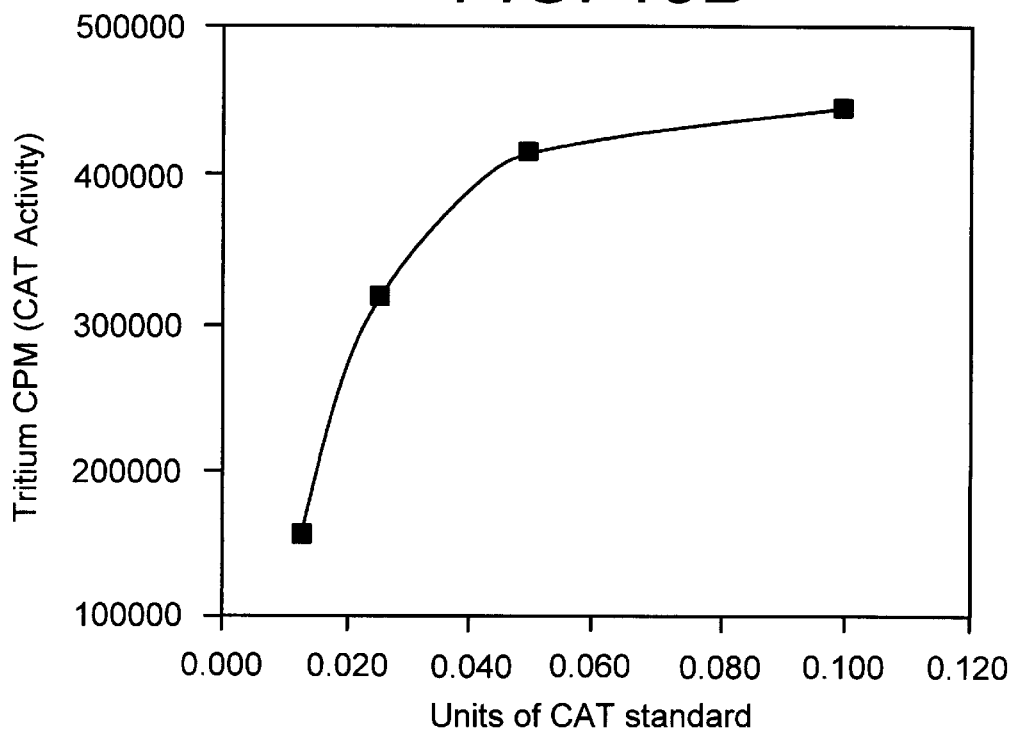

Because induction of RNA in previous studies approached 1000-fold, it might be expected that a reporter gene attached to these promoters would also be extremely high. The amount of radiolabeled chloramphenicol exceeded 500,000 cpm but a standard curve showed that around 400,000 cpm, the reaction begins to be substrate limiting after just three hours (FIG. 13). Background levels of CAT activity of –dex cells were only slightly higher than the background from xylene extraction at between 1,000 and 2,500 counts. Thus the highest fold induction accurately detectable would be around 500-fold or less.

Background becomes a major concern when calculating the fold-induction. There are two sources of background in these assays. First, transcription of the CAT gene on the pCAT®-BASIC vector with no insert and thus no promoter or enhancer sequences. This background will be referred to as "CAT background" because it represents the CAT activity produced by the presence of the gene regardless of promoter or enhancer sequences. Second, the xylene extraction of the n-butyrated chloramphenicol inevitably contains unreacted substrate. This basal level of tritium counts was measured by the negative controls (substrate with no cell extract). This background is referred to as "extraction background" because it represents the counts of tritium detected in the absence of enzyme due to the partition coefficient in xylene extractions.

For each type of MMTV LTR there was a response in transcription as detected by CAT activity to the presence of dexamethasone. Fold-induction was calculated as [CPM(+ dex)–CPM (extraction background)]÷[CPM(–dex)–CPM (extraction background)]=fold-induction. Using this formula, the induction, 2- to 7-fold, by the wild-type MMTV LTR was lower than the transcriptional induction reported earlier (7- to 20-fold). Correspondingly, induction by dexamethasone at the variant LTRs was considerably less than 1000 but still very high, 74.5- to 165-fold.

(Table 1). Fold induction is determined as raw counts of tritium labeled n-butyrated chloramphenicol excluding background from xylene extraction. Numbers represent the quotient of counts from transformed cells split and grown with and without dexamethasone (+dex/–dex).

| MMTV LTR TYPE | FOLD INDUCTION | CONSTRUCT OF GR1/GR4; GRE |
|---|---|---|
| VARIANT #1 | 74.5 (Average of 10 exp.) | 2 Repeats/Normal GRE (FIG. 12B) |
| VARIANT #2 | 165 (Average of 10 exp.) | 3 Repeats/No Normal GRE (FIG. 12D) |
| VARIANT #3 | 74.5 (Average of 8 exp.) | 2 Repeats/Normal GRE (FIG. 12B) |
| VARIANT #4 | 128 (Average of 10 exp.) | 3 Repeats/Normal GRE (FIG. 12C) |
| VARIANT #5 | 149 (Average of 8 exp.) | 3 Repeats/Normal GRE (FIG. 12C) |
| Wild Type (C3H) | 3.5 (Average of 10 exp.) | Normal GRE (FIG. 12A) |

Figure 14:
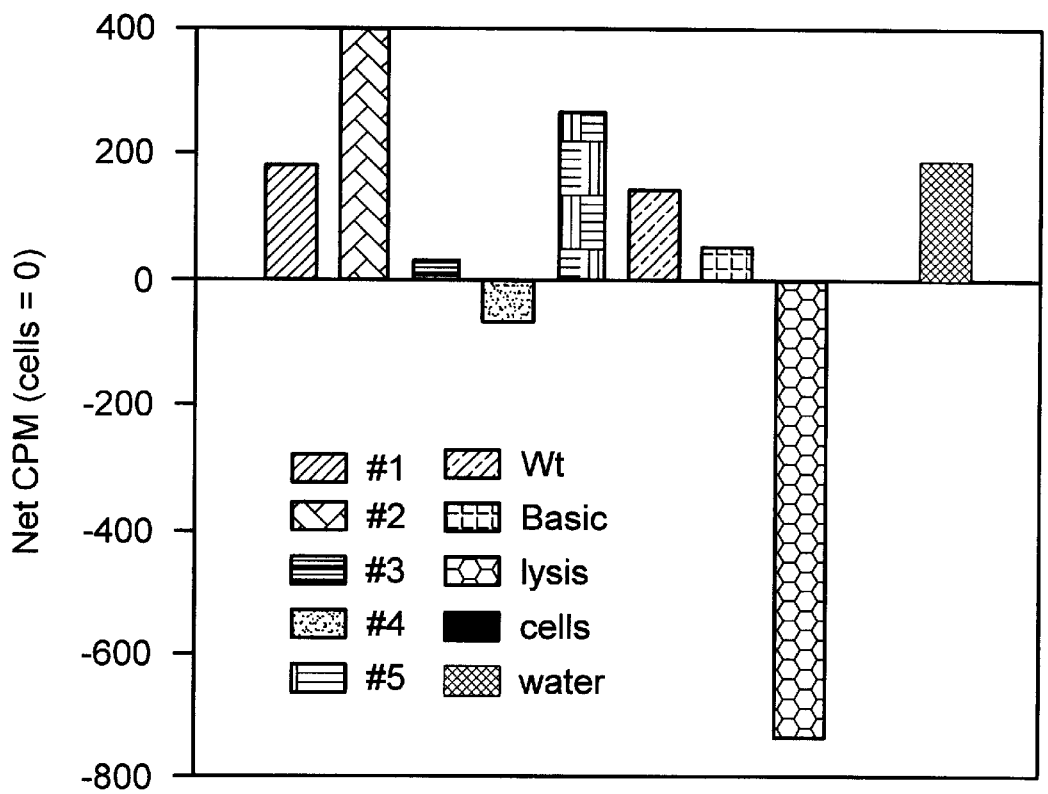
FIG. 14 is a graphic representation of the background counts and −dex control counts relative to the negative control. #1–190 5 in the legend represent variant #1-variant #5. Basic=pCAT-Basic vector, Lysis=Assay of substrates+ reporter lysis buffer, Cells=Assay on untransfected XC cells, Water=Assay on substrates+pure distilled water. The base or zero level is taken as the counts from cells and bars represent difference between that assay and the cells assay.
Figure 15:
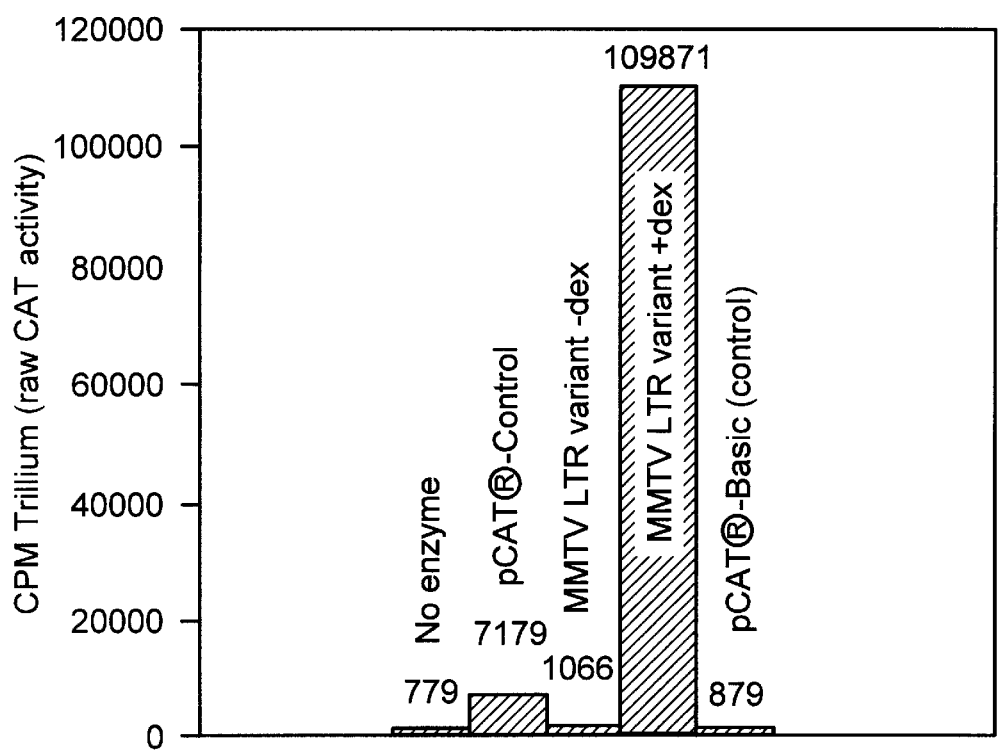
FIG. 15 is a comparison of promoters inducing CAT activity.

CAT assay background is a major limiting factor in measuring the fold-induction. Because the induction could span three orders of magnitude, several problems enter in. First, the –dex assays were all in the 1000–2000 CPM range. In this range, the standard deviation from the scintillation counter is nearly 5%. The extraction background and negative controls for each experiment were in the range of 900–1800 CPM. With CAT activity for the –dex controls so near background, it is difficult and in some cases impossible to accurately determine CAT activity for the –dex control FIG. 14 illustrates how near –dex controls are to the background control. In the assay represented in this graph, –dex control for variant #4 was actually lower than the extraction negative control (non-transfected cells lysed and assayed as all others). In assays performed on other days, the –dex control for variant #3 was lower than the negative control. A more sensitive method for measuring CAT activity is necessary to more accurately quantify the fold-induction. The +dex samples often become substrate limited before the –dex samples exceed levels detectable above the background. Adding more tritiated chloramphenicol helped overcome this effect, but as more substrate and labeled substrate was added, the background became higher. It is clear, however, that the fold-induction is extremely high for a eukaryotic system.

EXAMPLE 12

DNA Footprinting

Single-end Labeling

PCR was performed on the fragment of the LTR containing the GRE and the inserts. The same primers, G188 and G218 (see FIG. 4), used for sequencing were used with two methods of labeling the 3' end of the fragment. First, using polynucleotide kinase, primer G218 was labeled with $^{32}$p at the 5'-OH. This labeled primer was used in the PCR reaction just described and subsequently purified. Second, the PCR product of the above described reaction was treated for one minute with T4 DNA polymerase, whose 3' to 5' exonuclease activity removed approximately 30 to 50 bases on both 3' ends of the fragment. Radiolabeled dATP and the other three dNTP's were then added and incubated for fifteen minutes resulting in a blunt ended fragment with both 3' ends labeled.

The fragment was then cleaved with RsaI exonuclease resulting in two fragments, the smaller fragment was 170 bp, the larger fragment contained the different inserts and were between 388 and 619 bp in size. The restriction reaction was electrophoresed on a 1.6% agarose gel with 1× TAE. The larger fragment was cut directly from the gel with a razor blade and then expressed through a sterile syringe to disrupt the agarose. The DNA was then recovered from the agarose using "GENECLEAN II" (BIO 101 Inc., LaJolla, Calif.) and following instructions provided by manufacturer.

EXAMPLE 13
In Vitro DNA Binding Reaction

Footprinting reactions were performed as described by Freedman et al. ((1988) Nature 344(6182):543–546). Binding and DNase I reactions were done for samples at a time spaced temporally 15 seconds apart to maintain accuracy at each step. A sequencing reaction from the G218 primer was performed as described before on each LTR. Sequencing reaction and footprinting reactions with and without glucocorticoid receptor were electrophoresed on a 6% polyacrylamide denaturing gel at a constant power of 60 Watts for 3 hours. The gel was dried and exposed as described under sequencing.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

What is claimed is:

1. An isolated nucleic acid sequence which comprises at least one direct repeat of a fusion of the GR1 and the GR4 regions of a mammary tumor virus.

2. The isolated nucleic acid sequence of claim 1 wherein the mammary tumor virus is a murine mammary tumor virus.

3. The isolated nucleic acid sequence of claim 1 which comprises at least three direct repeats of a fusion of the GR1 and GR4 regions.

4. The isolated nucleic acid sequence of claim 1 which further includes, operably linked thereto, control elements which direct transcription of a DNA operably linked thereto, thereby rendering such control elements glucocorticoid hormone responsive.

5. An expression vector for the expression of a eukaryotic protein comprising the nucleic acid sequence of claim 1 and control elements which direct transcription of a DNA sequence encoding said eukaryotic protein operably linked in proper reading frame with said DNA sequences.

6. A vector which directs the transcription of a DNA sequence into an RNA transcript comprising the nucleic acid sequence of claim 1 and control elements which direct transcription of said DNA sequence.

7. The isolated nucleic acid sequence of claim 1 additionally comprising an intact glucocorticoid responsive element.

8. The isolated nucleic acid sequence of claim 2 wherein GR1 corresponds to the nucleic acid sequences spanning −214 to −156 to the transcriptional start site, and GR4 corresponds to the region spanning −91 to −72 to the transcriptional start site.

9. The isolated nucleic acid sequence of claim 2 wherein said sequence comprises a long terminal repeat.

10. The isolated nucleic acid sequence of claim 9 wherein said long terminal repeat comprises SEQ ID NO:4.

11. The isolated nucleic acid sequence of claim 9 wherein said long terminal repeat comprises SEQ ID NO:5.

12. The isolated nucleic acid sequence of claim 9 wherein said long terminal repeat comprises SEQ ID NO:6.

13. The isolated nucleic acid sequence of claim 9 wherein said long terminal repeat comprises SEQ ID NO:7.

14. The isolated nucleic acid sequence of claim 9 wherein said long terminal repeat comprises SEQ ID NO:8.

15. The isolated nucleic acid sequence of claim 4 wherein the DNA operably linked to the control elements is in the sense orientation.

16. The isolated nucleic acid sequence of claim 4 wherein the DNA operably linked to the control elements is in the antisense orientation.

17. The expression vector of claim 5 wherein the mammary tumor virus is a murine mammary tumor virus.

18. A method for the expression of a eukaryotic protein comprising transfecting a host cell with the expression vector of claim 5.

19. A host cell transfected with the expression vector of claim 5.

20. The expression vector of claim 17 wherein said sequence comprises a long terminal repeat.

21. The expression vector of claim 20 wherein said long terminal repeat comprises SEQ ID NO:4.

22. The expression vector of claim 20 wherein said long terminal repeat comprises SEQ ID NO:5.

23. The expression vector of claim 20 wherein said long terminal repeat comprises SEQ ID NO:6.

24. The expression vector of claim 20 wherein said long terminal repeat comprises SEQ ID NO:7.

25. The expression vector of claim 20 wherein said long terminal repeat comprises SEQ ID NO:8.

26. The vector of claim 6 wherein the mammary tumor virus is a murine mammary tumor virus.

27. A method for the transcription of a DNA sequence into an RNA transcript comprising transfecting a host cell with the vector of claim 6.

28. A host cell transfected with the vector of claim 6.

29. The vector of claim 6 wherein said RNA is an antisense RNA.

30. The vector of claim 6 wherein said RNA is a structural RNA.

31. The vector of claim 6 wherein said RNA is an RNA which has a function other than encoding a protein.

32. The vector of claim 26 wherein said sequence comprises a long terminal repeat.

33. The vector of claim 32 wherein said long terminal repeat comprises SEQ ID NO:4.

34. The vector of claim 32 wherein said long terminal repeat comprises SEQ ID NO:5.

35. The vector of claim 32 wherein said long terminal repeat comprises SEQ ID NO:6.

36. The vector of claim 32 wherein said long terminal repeat comprises SEQ ID NO:7.

37. The vector of claim 32 wherein said long terminal repeat comprises SEQ ID NO:8.

38. A method for the transcription of a DNA sequence into an RNA transcript comprising transfecting a host cell with the vector of claim 29.

39. A host cell transfected with the vector of claim 29.

40. A method for the transcription of a DNA sequence into an RNA transcript comprising transfecting a host cell with the vector of claim 30.

41. A host cell transfected with the vector of claim 30.

42. A method for the transcription of a DNA sequence into an RNA transcript comprising transfecting a host cell with the vector of claim 31.

43. A host cell transfected with the vector of claim 31.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
AGAACANNNT GTTCT                                                          15
```

( 2 ) INFORMATION FOR SEQ ID NO:2:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
CGGTTCCCAG GGCTTAAGTA AGTTTTTGGT TACAAACTGT TCTTAAAACG AGGATGTGAC         60
TCCTATGTTC TTTTGGAA                                                       78
```

( 2 ) INFORMATION FOR SEQ ID NO:3:

( i ) SEQUENCE CHARACTERISTICS:
        ( A ) LENGTH: 447 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
CGTGAAAGAC TCGCCAGAGC TAGACCTCCT TGGTATATGT TGTCTCAAGA AGAAAAAGAC         60
GACATGAAAC AACAGGTACA TGATTATATT TATCTAGGAA CAAGAATGCA CTTTTGGGGA        120
AAGATTTTCC ATACCAAGGA GGGGACAGTG GCTAGACTAA TAGAACATTA TTCTACAAAA        180
ACTTATGACA TGAGTTATTA TAAATAGCCT TTATTGGCCC AACCTTGCGG TTCCCAGGGC        240
TTAAGTAAGT TTTTGGTTAC AAACTGTTCT TAAAACGAGG ATGTGAGACA AGTGGTTTCC        300
TGACTTGGTT TGGTATCAAA GGTTCTGATC TGAGCTCTGA GTGTTCTATT TTCCTATGTT        360
CTTTTGGAAT TTATCCAAAT CTTATGTAAA TGCTTATGTA AACCAAGATA TAAAAGAGTG        420
CTGATTTTTT TGAGTAAACT TGCAACA                                            447
```

( 2 ) INFORMATION FOR SEQ ID NO:4:

( i ) SEQUENCE CHARACTERISTICS:
        ( A ) LENGTH: 602 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

| | | | | | | |
|---|---|---|---|---|---|---|
| CGTGAAAGAC | TCGCCAGAGC | TAGACCTCCT | TGGTGTATGT | TGTCTCAAGA | AGAAAAAGAC | 60 |
| GACATGAAAC | AACAGGTACA | TGATTATATT | TATCTAGGAA | CAAGAATGCA | CTTTTGGGGA | 120 |
| AAGATTTTCC | ATACCAAGGA | GGGGACAGTG | GCTAGACTAA | TAGAACATTA | TTCTACAAAA | 180 |
| ACTTATGACA | TGAGTTATTA | TAAATAGCCT | TTATTGGCCC | AACCTTGCGG | TTCCCAGGGC | 240 |
| TTAAGTAAGT | TTTTGGTTAC | AAACTGTTCT | TAAAACGAGG | ATGTGACTCC | TATGTTCTTT | 300 |
| TGAACGGTTC | CCAGGGCTTA | AGTAAGTTTT | TGGTTACAAA | CTGTTCTTAA | AACGAGGATG | 360 |
| TGACTCCTAT | GTTCTTTTGG | AACGGTTCCC | AGGGCTTAAG | TAAGTCTTTG | GTTACAAACT | 420 |
| GTTCTTAAAA | CGAGGATGTG | AGACAAGTGG | TTTCCTGACT | TGGTTTGGTA | TCAAAGGTTC | 480 |
| TGATCTGAGC | TCTGAGTGTT | CTATTTTCCT | ATGTTCTTTT | GGAATTTATC | CAAATCTTAT | 540 |
| GTAAATGCTT | ATGTAAACCA | AGATATAAAA | GAGTGCTGAT | TTTTTTGAGT | AAACTTGCAA | 600 |
| CA | | | | | | 602 |

( 2 ) INFORMATION FOR SEQ ID NO:5:

( i ) SEQUENCE CHARACTERISTICS:
        ( A ) LENGTH: 528 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

| | | | | | | |
|---|---|---|---|---|---|---|
| CGTGAAAGAC | TCGCCAGAGC | TAGACCTCCT | TGGTATATGT | TGAAAAAGAC | GACATGAAAC | 60 |
| AACAGGTACA | TGATTATATT | TATCTAGGAA | CAAGAATGCA | CTTTTGGGGA | AAGATTTTCC | 120 |
| ATACCAAGGA | GGGGACAGTG | GCTAGACTAA | TAGAACATTA | TTCTACAAAA | ACTTATGACA | 180 |
| TGAGTTATTA | TAAATAGCCT | TTATTGGCCC | AACCTTGCGG | TTCCCAGGGC | TTAAGTAAGT | 240 |
| TTTTGGTTAC | AAACTGTTCT | TAAAACGAGG | ATGTGACTCC | TATGTTCTTT | TGAACGGTTC | 300 |
| CCAGGGCTTA | AGTAAGTTTT | TGGTTACAAA | CTGTTCTTAA | AACGAGGATG | TGACTCCTAT | 360 |
| GTTCTTTTGG | AACGGTTCCC | AGGGCTTAAG | TAAGTCTTTG | GTTACAAACT | GTTCTTAAAA | 420 |
| CGAGGATGTG | ACTCCTATGT | TCTTTTGGAA | TTTATCCAAA | TCTTATGTAA | ATGCTTATGT | 480 |
| AAACCAAGAT | ATAAAGAGT | GCTGATTTTT | TTGAGTAAAC | TTGCAACA | | 528 |

( 2 ) INFORMATION FOR SEQ ID NO:6:

( i ) SEQUENCE CHARACTERISTICS:
        ( A ) LENGTH: 603 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

| | | | | | |
|---|---|---|---|---|---|
| CGTGAAAGAC | TCGCCAGAGC | TAGACCTCCT | TGGTGTATGT | TGTCTCAAGA | AGAAAAAGAC | 60 |
| GACATGAAAC | AACAGGTACA | TGATTATATT | TATCTAGGAA | CAAGAATGCA | CTTTTGGGGA | 120 |
| AAGATTTTCC | ATACCAAGGA | GGGGACAGTG | GCTAGACTAA | TAGAACATTA | TTCTACAAAA | 180 |
| ACTTATGACA | TGAGTTATTA | TAAATAGCCT | TTATTGGCCC | AACCTTGCGG | TTCCCAGGGC | 240 |
| TTAAGTAAGT | TTTTGGTTAC | AAACTGTTCT | TAAAACGAGG | ATGTGACTCC | TATGTTCTTT | 300 |
| TGGAACGGTT | CCCAGGGCTT | AAGTAAGTTT | TTGGTTACAA | ACTGTTCTTA | AAACGAGGAT | 360 |
| GTGACTCCTA | TGTTCTTTTG | GAACGGTTCC | CAGGGCTTAA | GTAAGTTTTT | GGTTACAAAC | 420 |
| TGTTCTTAAA | ACGAGGATGT | GAGACAAGTG | GTTTCCTGAC | TTGGTTTGGT | ATCAAAGGTT | 480 |
| CTGATCTGAG | CTCTGAGTGT | CTATTTTCC | TATGTTCTTT | TGGAATTTAT | CCAAATCTTA | 540 |
| TGTAAATGCT | TATGTAAACC | AAGATATAAA | AGAGTGCTGA | TTTTTTGAG | TAAACTTGCA | 600 |
| ACA | | | | | | 603 |

( 2 ) INFORMATION FOR SEQ ID NO:7:

( i ) SEQUENCE CHARACTERISTICS:
        ( A ) LENGTH: 737 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

| | | | | | |
|---|---|---|---|---|---|
| CGTGAAAGAC | TCGCCAGAGC | TAGACCTCCT | TGGTATATGT | TGTCTCAAGA | AGAAAAAGAC | 60 |
| GACATGAAAC | AACAGGTACA | TGATTATATT | TATCTAGGAA | CAAGAATGCA | CTTTTGGGGA | 120 |
| AAGATTTTCC | ATACCAAGGA | GGGGACAGTG | GCTAGACAAT | AGAACATTAT | TCTACAAAAA | 180 |
| CTTATGACAT | GAGTTATTAT | AAATAGCCTT | TATTGGCCCA | ACCTTGCGGT | TCCCAGGGCT | 240 |
| TAGTAAGTTT | TTGGTTACAA | ACTGTTCTTA | AAACGAGGAT | GTGACTCCTA | TGTTCTTTGT | 300 |
| TAGTAAGTTT | TTGGTTACAA | ACTGTTCTTA | AAACGAGGAT | GTGACTCCTA | TGTTCTTTGG | 360 |
| AACGGTTCCC | AGGGCTTAAG | TAAGTTTTG | GTTACAAACT | GTTCTTAAAA | CGAGGATGTG | 420 |
| ACTCCTATGT | TCTTTTGAAC | GGTTCCCAGG | GCTTAAGTAA | GTTTTGGTT | ACAAACTGTT | 480 |
| CTTAAAACGA | GGATGTGACT | CCTATGTTCT | TTTGGAACGG | TTCCCAGGGC | TTAAGTAAGT | 540 |
| TTTTGGTTAC | AAACTGTTCT | TAAAACGAGG | ATGTGAGACA | AGTGGTTTCC | TGACTTGGTT | 600 |
| TGGTATCAAA | GGTTCTGATC | TGAGCTCTGA | GTGTTCTATT | TTCCTATGTT | CTTTTGGAAT | 660 |
| TTATCCAAAT | CTTATGTAAA | TGCTTATGTA | AACCAAGATA | TAAAAGAGTG | CTGATTTTTT | 720 |
| TGAGTAAACT | TGCAACA | | | | | 737 |

( 2 ) INFORMATION FOR SEQ ID NO:8:

( i ) SEQUENCE CHARACTERISTICS:
        ( A ) LENGTH: 737 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

| | | | | | |
|---|---|---|---|---|---|
| CGTGAAAGAC | TCGCCAGAGC | TAGACCTCCT | TGGTATATGT | TGTCTCAAGA | AGAAAAAGAC | 60 |
| GACATGAAAC | AACAGGTACA | TGATTATATT | TATCTAGGAA | CAAGAATGCA | CTTTTGGGGA | 120 |
| AAGATTTTCC | ATACCAAGGA | GGGGACAGTG | GCTAGACAAT | AGAACATTAT | TCTACAAAAA | 180 |

| | | | | | |
|---|---|---|---|---|---|
| CTTATGACAT | GAGTTATTAT | AAATAGCCTT | TATTGGCCCA | ACCTTGCGGT | TCCCAGGGCA | 240 |
| CTTATGACAT | GAGTTATTAT | AAATAGCCTT | TATTGGCCCA | ACCTTGCGGT | TCCCAGGGCT | 300 |
| TAGTAAGTTT | TTGGTTACAA | ACTGTTCTTA | AAACGAGGAT | GTGACTCCTA | TGTTCTTTGG | 360 |
| AACGGTTCCC | AGGGCTTAAG | TAAGTTTTTG | GTTACAAACT | GTTCTTAAAA | CGAGGATGTG | 420 |
| ACTCCTATGT | TCTTTTGAAC | GGTTCCCAGG | GCTTAAGTAA | GTTTTTGGTT | ACAAACTGTT | 480 |
| CTTAAAACGA | GGATGTGACT | CCTATGTTCT | TTTGGAACGG | TTCCCAGGGC | TTAAGTAAGT | 540 |
| TTTTGGTTAC | AAACTGTTCT | TAAAACGAGG | ATGTGAGACA | AGTGGTTTCC | TGACTTGGTT | 600 |
| TGGTATCAAA | GGTTCTGATC | TGAGCTCTGA | GTGTTCTATT | TTCCTATGTT | CTTTTGGAAT | 660 |
| TTATCCAAAT | CTTATGTAAA | TGCTTATGTA | AACCAAGATA | TAAAAGAGTG | CTGATTTTTT | 720 |
| TGAGTAAACT | TGCAACA | | | | | 737 |

(2) INFORMATION FOR SEQ ID NO:9:

(i) SEQUENCE CHARACTERISTICS:
(A) LENGTH: 1464 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

| | | | | | |
|---|---|---|---|---|---|
| ATGCCGCGCC | TGCAGCAGAA | ATGGTTGAAC | TCCCGAGAGT | GTCCTACACC | TAGGGAGAA | 60 |
| GCAGCCAAGG | GGTTGTTTCC | CACCAAGGAC | GACCCGTCTG | CGCACAAACG | GGTGAGCCCA | 120 |
| TCAGACAAAG | ACATATTCAT | TCTCTGCTGC | AAACTTGGCA | TAGCTCTGCT | TTGCCTGGGG | 180 |
| CTATTGGGGG | AAGTTGCGGT | TCGTGCTCGC | AGGGCTCTCA | CCCTTGACTC | TTTTAATAGC | 240 |
| TCTTCTGTGC | AAGATTACAA | TCTAAACAAT | TCGGAGAACT | CGACCTTCCT | CCTGAGGCAA | 300 |
| GGACCACAGC | CAACTTCCTC | TTACAAGCCG | CATCGATTTT | GTCCTTCAGA | AATAGAAATA | 360 |
| AGAATGCTTG | CTAAAAATTA | TATTTTTACC | AATAAGACCA | ATCCAATAGG | TAGATTATTA | 420 |
| GTTACTATGT | TAAGAAATGA | ATCATTATCT | TTTAGTACTA | TTTTTACTCA | AATTCAGAAG | 480 |
| TTAGAAATGG | GAATAGAAAA | TAGAAAGAGA | CGCTCAACCT | CAATTGAAGA | ACAGGTGCAA | 540 |
| GGACTATTGA | CCACAGGCCT | AGAAGTAAAA | AAGGGAAAAA | AGAGTGTTTT | TGTCAAAATA | 600 |
| GGAGACAGGT | GGTGGCAACT | AGGGACTTAT | AGGGGACCTT | ACATCTACAG | ACCAACAGAT | 660 |
| GCCCCCTTAC | CATATACAGG | AAGATATGAC | TTAAATTGGG | ATAGGTGGT | TACAGTCAAT | 720 |
| GGCTATAAAG | TGTTATATAG | ATCCCTCCCT | TTTCGTGAAA | GACTCGCCAG | AGCTAGACCT | 780 |
| CCTTGGTGTA | TGTTGTCTCA | AGAAGAAAAA | GACGACATGA | AACAACAGGT | ACATGATTAT | 840 |
| ATTTATCTAG | GAACAGGAAT | GCACTTTTGG | GGAAAGATTT | TCCATACCAA | GGAGGGGACA | 900 |
| GTGGCTGGAC | TAATAGAACA | TTATTCTCCA | AAAACTTATG | GCATGAGTTA | TTATGAATAG | 960 |
| CCTTTATTGG | CCCAACCTTG | CGGTTCCAG | GCTTAAGTA | AGTTTTGGT | TACAAACTGT | 1020 |
| TCTTAAAACG | AGGATGTGAG | ACAAGTGGTT | TCCTGACTTG | GTTTGGTATC | AAAGGTTCTG | 1080 |
| ATCTGAGCTC | TGAGTGTTCT | ATTTTCCTAT | GTTCTTTTGG | AATTTATCCA | AATCTTATGT | 1140 |
| AAATGCTTAT | GTAAACCAAG | ATATAAAAGA | GTGCTGATTT | TTTGAGTAA | ACTTGCAACA | 1200 |
| GTTCCTAACA | TTCACCTCTT | GTGTGTTTGT | GTCTGTTCGC | CATCCCGTCT | CCGCTCGTCA | 1260 |
| CTTATCCTTC | ACTTTCCTGC | GGGTCCCCCC | GCAGACCCCG | GCGACCTCAG | GTCGGCCGAC | 1320 |
| TGCGGCAGCT | GGCGCCCGAA | CAGGGACCCC | TCGGATAAGT | GACCCTTGTC | TCTATTTCTA | 1380 |
| CTATTTGGTG | TTTGTCTTGT | ATTGTCTCTT | TCTTGTCTTT | CTATCATCAC | AAGAGCGGAA | 1440 |

CGGACTCACC ATAGGGAGCT GCAG                                              1464

( 2 ) INFORMATION FOR SEQ ID NO:10:

( i ) SEQUENCE CHARACTERISTICS:
        ( A ) LENGTH: 1621 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
ATGCCGCGCC TGCAGCAGAA ATGGTTGAAC TCCCGAGAGT GTCCTACACC TAGGGGAGAA      60
GCAGCCAAGG GGTTGTTTCC CACCAAGGAC GACCCGTCTG CGCACAAACG GGTGAGCCCA     120
TCAGACAAAG ACATATTCAT TCTCTGCTGC AAACTTGGCA TAGCTCTGCT TTGCCTGGGG     180
CTATTGGGGG AAGTTGCGGT TCGTGCTCGC AGGGCTCTCA CCCTTGACTC TTTTAATAGC     240
TCTTCTGTGC AAGATTACAA TCTAAACAAT TCGGAGAACT CGACCTTCCT CCTGAGGCAA     300
GGACCACAGC CAACTTCCTC TTACAAGCCG CATCGATTTT GTCCTTCAGA AATAGAAATA     360
AGAATGCTTG CTAAAAATTA TATTTTTACC AATAAGACCA ATCCAATAGG TAGATTATTA     420
GTTACTATGT TAAGAAATGA ATCATTATCT TTTAGTACTA TTTTACTCA AATTCAGAAG      480
TTAGAAATGG GAATAGAAAA TAGAAAGAGA CGCTCAACCT CAATTGAAGA ACAGGTGCAA     540
GGACTATTGA CCACAGGCCT AGAAGTAAAA AAGGGAAAAA AGAGTGTTTT TGTCAAAATA     600
GGAGACAGGT GGTGGCAACT AGGGACTTAT AGGGACCTT ACATCTACAG ACCAACAGAT      660
GCCCCCTTAC CATATACAGG AAGATATGAC TTAAATTGGG ATAGGTGGGT TACAGTCAAT     720
GGCTATAAAG TGTTATATAG ATCCCTCCCT TTTCGTGAAA GACTCGCCAG AGCTAGACCT     780
CCTTGGTGTA TGTTGTCTCA AGAAGAAAAA GACGACATGA AACAACAGGT ACATGATTAT     840
ATTTATCTAG AACAGGAAT GCACTTTTGG GGAAAGATTT TCCATACCAA GGAGGGGACA      900
GTGGCTAGAC TAATAGAACA TTATTCTACA AAAACTTATG ACATGAGTTA TTATAAATAG    960
CCTTTATTGG CCCAACCTTA GACGGTTCCC AGGGCTTAAG TAAGTTTTTG GTTACAAACT    1020
GTTCTTAAAA CGAGGATGTG ACTCCTATGT TCTTTTGAAC GGTTCCCAGG GCTTAAGTAA    1080
GTTTTTGGTT ACAAACTGTT CTTAAAACGA GGATGTGACT CCTATGTTCT TTTGGAACGG    1140
TTCCCAGGGC TTAAGTAAGT CTTTGGTTAC AAACTGTTCT TAAAACGAGG ATGTGAGACA    1200
AGTGGTTTCC TGACTTGGTT TGGTATCAAA GGTTCTGATC TGAGCTCTGA GTGTTCTATT    1260
TTCCTATGTT CTTTTGGAAT TTATCCAAAT CTTATGTAAA TGCTTATGTA AACCAAGATA    1320
TAAAAGAGTG CTGATTTTTT TGAGTAAACT TGCAACAGTT CCTAACATTC ACCTCTTGTG    1380
TGTTTGTGTC TGTTCGCCAT CCCGTCTCCG CTCGTCACTT ATCCTTCACT TTCCTGCGGG    1440
TCCCCCCGCA GACCCCGGCG ACCTCAGGTC GGCCGACTGC GGCAGCTGGC GCCCGAACAG    1500
GGACCCCTCG GATAAGTGAC CCTTGTCTCT ATTTCTACTA TTTGGTGTTT GTCTTGTATT    1560
GTCTCTTTCT TGTCTTTCTA TCATCACAAG AGCGGAACGG ACTCACCATA GGGAGCTGCA    1620
G                                                                   1621
```

( 2 ) INFORMATION FOR SEQ ID NO:11:

( i ) SEQUENCE CHARACTERISTICS:
        ( A ) LENGTH: 1546 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

| | | | | | |
|---|---|---|---|---|---|
| ATGCCGCGCC | TGCAGCAGAA | ATGGTTGAAC | TCCCGAGAGT | GTCCTACACC | TAGGGGAGAA | 60 |
| GCAGCCAAGG | GGTTGTTTCC | CACCAAGGAC | GACCCGTCTG | CGCACAAACG | GGTGAGCCCA | 120 |
| TCAGACAAAG | ACATATTCAT | TCTCTGCTGC | AAACTTGGCA | TAGCTCTGCT | TTGCCTGGGG | 180 |
| CTATTGGGGG | AAGTTGCGGT | TCGTGCTCGC | AGGGCTCTCA | CCCTTGACTC | TTTTAATAGC | 240 |
| TCTTCTGTGC | AAGATTACAA | TCTAAACAAT | TCGGAGAACT | CGACCTTCCT | CCTGAGGCAA | 300 |
| GGACCACAGC | CAACTTCCTC | TTACAAGCCG | CATCGATTTT | GTCCTTCAGA | AATAGAAATA | 360 |
| AGAATGCTTG | CTAAAAATTA | TATTTTTACC | AATAAGACCA | ATCCAATAGG | TAGATTATTA | 420 |
| GTTACTATGT | TAAGAAATGA | ATCATTATCT | TTTAGTACTA | TTTTTACTCA | AATTCAGAAG | 480 |
| TTAGAAATGG | GAATAGAAAA | TAGAAAGAGA | CGCTCAACCT | CAATTGAAGA | ACAGGTGCAA | 540 |
| GGACTATTGA | CCACAGGCCT | AGAAGTAAAA | AAGGGAAAAA | AGAGTGTTTT | TGTCAAAATA | 600 |
| GGAGACAGGT | GGTGGCAACT | AGGGACTTAT | AGGGGACCTT | ACATCTACAG | ACCAACAGAT | 660 |
| GCCCCCTTAC | CATATACAGG | AAGATATGAC | TTAAATTGGG | ATAGGTGGGT | TACAGTCAAT | 720 |
| GGCTATAAAG | TGTTATATAG | ATCCCTCCCT | TTTCGTGAAA | GACTCGCCAG | AGCTAGACCT | 780 |
| CCTTGGTGTA | TGTTGAAAAA | GACGACATGA | AACAACAGGT | ACATGATTAT | ATTTATCTAG | 840 |
| GAACAGGAAT | GCACTTTTGG | GGAAAGATTT | TCCATACCAA | GGAGGGGACA | GTGGCTGGAC | 900 |
| TAATAGAACA | TTATTCTCCA | AAAACTTATG | GCATGAGTTA | TTATGAATAG | CCTTTATTGG | 960 |
| CCCAACCTTG | CGGTTCCCAG | GGCTTAAGTA | AGTTTTTGGT | TACAAACTGT | TCTTAAAACG | 1020 |
| AGGATGTGAC | TCCTATGTTC | TTTTGGAACG | GTTCCCAGGG | CTTAAGTAAG | TTTTTGGTTA | 1080 |
| CAAACTGTTC | TTAAAACGAG | GATGTGACTC | CTATGTTCTT | TTGGAACGGT | TCCCAGGGCT | 1140 |
| TAAGTAAGTT | TTTGGTTACA | AACTGTTCTT | AAAACGAGGA | TGTGACTCCT | ATGTTCTTTT | 1200 |
| GGAATTTATC | CAAATCTTAT | GTAAATGCTT | ATGTAAACCA | AGATATAAAA | GAGTGCTGAT | 1260 |
| TTTTTTGAGT | AAACTTGCAA | CAGTTCCTAA | CATTCACCTC | TTGTGTGTTT | GTGTCTGTTC | 1320 |
| GCCATCCCGT | CTCCGCTCGT | CACTTATCCT | TCACTTTCCT | GCGGGTCCCC | CCGCAGACCC | 1380 |
| CGGCGACCTC | AGGTCGGCCG | ACTGCGGCAG | CTGGCGCCCG | AACAGGGACC | CCTCGGATAA | 1440 |
| GTGACCCTTG | TCTCTATTTC | TACTATTTGG | TGTTTGTCTT | GTATTGTCTC | TTTCTTGTCT | 1500 |
| TTCTATCATC | ACAAGAGCGG | AACGGACTCA | CCATAGGGAG | CTGCAG | | 1546 |

( 2 ) INFORMATION FOR SEQ ID NO:12:

( i ) SEQUENCE CHARACTERISTICS:
        ( A ) LENGTH: 1616 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

| | | | | | |
|---|---|---|---|---|---|
| ATGCCGCGCC | TGCAGCAGAA | ATGGTTGAAC | TCCCGAGAGT | CTCCTACACC | TAGGGGAGAA | 60 |
| GCAGCCAAGG | GGTTGTTTCC | CACCAAGGAC | GACCCGTCTG | CGCACAAACG | GGTGAGCCCA | 120 |
| TCAGACAAAG | ACATATTCAT | TCTCTGCTGC | AAACTTGGCA | TAGCTCTGCT | TTGCCTGGGG | 180 |
| CTATTGGGGG | AAGTTGCGGT | TCGTGCTCGC | AGGGCTCTCA | CCCTTGACTC | TTTTAATAGC | 240 |
| TCTTCTGTGC | AAGATTACAA | TCTAAACAAT | TCGGAGAACT | CGACCTTCCT | CCTGAGGCAA | 300 |

| | | | | | |
|---|---|---|---|---|---|
| GGACCACAGC | CAACTTCCTC | TTACAAGCCG | CATCGATTTT | GTCCTTCAGA | AATAGAAATA | 360 |
| AGAATGCTTG | CTAAAAATTA | TATTTTTACC | AATAAGACCA | ATCCAATAGG | TAGATTATTA | 420 |
| GTTACTATGT | TAAGAAATGA | ATCATTATCT | TTTAGTACTA | TTTTTACTCA | AATTCAGAAG | 480 |
| TTAGAAATGG | GAATAGAAAA | TAGAAAGAGA | CGCTCAACCT | CAATTGAAGA | ACAGGTGCAA | 540 |
| GGACTATTGA | CCACAGGCCT | AGAAGTAAAA | AAGGGAAAAA | AGAGTGTTTT | TGTCAAAATA | 600 |
| GGAGACAGGT | GGTGGCAACT | AGGGACTTAT | AGGGGACCTT | ACATCTACAG | ACCAACAGAT | 660 |
| GCCCCCTTAC | CATATACAGG | AAGATATGAC | TTAAATTGGG | ATAGGTGGGT | TACAGTCAAT | 720 |
| GGCTATAAAG | TGTTATATAG | ATCCCTCCCT | TTTCGTGAAA | GACTCGCCAG | AGCTAGACCT | 780 |
| CCTTGGTGTA | TGTTGTCTCA | AGAAGAAAAA | GACGACATGA | AACAACAGGT | ACATGATTAT | 840 |
| ATTTATCTAG | GAACAAGAAT | GCACTTTTGG | GGAAAGATTT | TCCATACCAA | GGAGGGGACA | 900 |
| GTGGCTAGAC | TAATAGAACA | TTATTCTACA | AAAACTTATG | ACATGAGTTA | TTATAAATAG | 960 |
| CCTTTATTGG | CCCAACCTTG | CGGTTCCCAG | GGCTTAAGTA | AGTTTTGGTT | ACAAACTGTT | 1020 |
| CTTAAAACGA | GGATGTGACT | CCTATCTTTT | GGAACGGTTC | CCANGGCTTA | AGTAAGGTTT | 1080 |
| TGGTTACAAA | CTGTTCTTAA | AACGAGGATG | TGACTCCTAT | GTTCTTTTGG | AACGGTTCCC | 1140 |
| AGGGCTTAAG | TAAGTTTTTG | GTTACAAACG | GTTCTTAAAA | CGAGGATGTG | AGACAAGTGG | 1200 |
| TTTCCTGACT | TGGTTTGGTA | TCAAAGGTTC | TGATCTGAGC | TCTGAGTGTT | CTATTTTCCT | 1260 |
| ATGTTCTTTT | GGAATTTATC | CAAATCTTAT | GTAAATGCTT | ATGTAAACCA | AGATATAAAA | 1320 |
| GAGTGCTGAT | TTTTTTGAGT | AAACTTGCAA | CAGTTCCTAA | CATTCACCTC | TTGTGTGTTT | 1380 |
| GTGTCTGTTC | GCCATCCCGT | CTCCGCTCGT | CACTTATCCT | TCACTTTCCT | GCAGGTCCCC | 1440 |
| CCGCAGACCC | CGGCGACCTC | AGGTCGGCCG | ACTGCGGCAG | CTGGCGCCCG | AACAGGGACC | 1500 |
| CCTCGGATAA | GTGACCCTTG | TCTCTATTTC | TACTATTTGG | TGTTTGTCTT | GTATTGTCTC | 1560 |
| TTTCTTGTCT | TTCTATCATC | ACAAGAGCGG | AACGGACTCA | CCATAGGGAG | CTGCAG | 1616 |

(2) INFORMATION FOR SEQ ID NO:13:

(i) SEQUENCE CHARACTERISTICS:
        (A) LENGTH: 1693 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

| | | | | | |
|---|---|---|---|---|---|
| ATGCCGCGCC | TGCAGCAGAA | ATGGTTGAAC | TCCCGAGAGT | GTCCTACACC | TAGGGGAGAA | 60 |
| GCAGCCAAGG | GGTTGTTTCC | CACCAAGGAC | GACCCGTCTG | CGCACAAACG | GGTGAGCCCA | 120 |
| TCAGACAAAG | ACATATTCAT | TCTCTGCTGC | AAACTTGGCA | TAGCTCTGCT | TTGCCTGGGG | 180 |
| CTATTGGGGG | AAGTTGCGGT | TCGTGCTCGC | AGGGCTCTCA | CCCTTGACTC | TTTTAATAGC | 240 |
| TCTTCTGTGC | AAGATTACAA | TCTAAACAAT | TCGGAGAACT | CGACCTTCCT | CCTGAGGCAA | 300 |
| GGACCACAGC | CAACTTCCTC | TTACAAGCCG | CATCGATTTT | GTCCTTCAGA | AATAGAAATA | 360 |
| AGAATGCTTG | CTAAAAATTA | TATTTTTACC | AATAAGACCA | ATCCAATAGG | TAGATTATTA | 420 |
| GTTACTATGT | TAAGAAATGA | ATCATTATCT | TTTAGTACTA | TTTTTACTCA | AATTCAGAAG | 480 |
| TTAGAAATGG | GAATAGAAAA | TAGAAAGAGA | CGCTCAACCT | CAATTGAAGA | ACAGGTGCAA | 540 |
| GGACTATTGA | CCACAGGCCT | AGAAGTAAAA | AAGGGAAAAA | AGAGTGTTTT | TGTCAAAATA | 600 |
| GGAGACAGGT | GGTGGCAACT | AGGGACTTAT | AGGGGACCTT | ACATCTACAG | ACCAACAGAT | 660 |
| GCCCCCTTAC | CATATACAGG | AAGATATGAC | TTAAATTGGG | ATAGGTGGGT | TACAGTCAAT | 720 |

| | | | | | |
|---|---|---|---|---|---|
| GGCTATAAAG | TGTTATATAG | ATCCCTCCCT | TTTCGTGAAA | GACTCGCCAG | AGCTAGACCT | 780 |
| CCTTGGTATA | TGTTGTCTCA | AGAAGAAAAA | GACGACATGA | AACAACAGGT | ACATGATTAT | 840 |
| ATTTATCTAG | GAACAAGAAT | GCACTTTTGG | GGAAAGATTT | CCATACCAAG | GAGGGGACAG | 900 |
| TGGCTAGACA | ATAGAACATT | ATTCTACAAA | AACTTATGAC | ATGAGTTATT | ATAAATAGCC | 960 |
| TTTATTGGCC | CAACCTTGCG | GTTCCCAGGG | CTTAGTAAGT | TTTTGGTTAC | AAACTGTTCT | 1020 |
| TAAAACGAGG | ATGTGACTCC | TATGTTCTTT | GGAACGGTTC | CCAGGGCTTA | AGTAAGTTTT | 1080 |
| TGGTTACAAA | CTGTTCTTAA | AACGAGGATG | TGACTCCTAT | GTTCTTTTGG | ACGGTTCCCA | 1140 |
| GGGCTTAAGT | AAGTTTTTGG | TTACAAACTG | TTCTTAAAAC | GAGGATGTGA | CTCCTATGTT | 1200 |
| CTTTTGGAAC | GGTTCCCAGG | GCTTAAGTAA | GTTTTGGTT | ACAAACTGTT | CTTAAAACGA | 1260 |
| GGATGTGAGA | CAAGTGGTTT | CCTGACTTGG | TTTGGTATCA | AAGGTTCTGA | TCTGAGCTCT | 1320 |
| GAGTGTTCTA | TTTTCCTATG | TTCTTTTGGA | ATTTATCCAA | ATCTTATGTA | AATGCTTATG | 1380 |
| TAAACCAAGA | TATAAAGAG | TGCTGATTTT | TTTGAGTAAA | CTTGCAACAG | TTCCTAACAT | 1440 |
| TCACCTCTTG | TGTGTTTGTG | TCTGTTCGCC | ATCCCGTCTC | CGCTCGTCAC | TTATCCTTCA | 1500 |
| CTTTCCTGCG | GGTCCCCCCG | CAGACCCCGG | CGACCTCAGG | TCGGCCGACT | GCGGCAGCTG | 1560 |
| GCGCCCGAAC | AGGGACCCCT | CGGATAAGTG | ACCCTTGTCT | CTATTTCTAC | TATTTGGTGT | 1620 |
| TTGTCTTGTA | TTGTCTCTTT | CTTGTCTTTC | TATCATCACA | AGAGCGGAAC | GGACTCACCA | 1680 |
| TAGGGAGCTG | CAG | | | | | 1693 |

(2) INFORMATION FOR SEQ ID NO:14:

(i) SEQUENCE CHARACTERISTICS:
        (A) LENGTH: 1693 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

| | | | | | |
|---|---|---|---|---|---|
| ATGCCGCGCC | TGCAGCAGAA | ATGGTTGAAC | TCCCGAGAGT | GTCCTACACC | TAGGGGAGAA | 60 |
| GCAGCCAAGG | GGTTGTTTCC | CACCAAGGAC | GACCCGTCTG | CGCACAAACG | GGTGAGCCCA | 120 |
| TCAGACAAAG | ACATATTCAT | TCTCTGCTGC | AAACTTGGCA | TAGCTCTGCT | TTGCCTGGGG | 180 |
| CTATTGGGGG | AAGTTGCGGT | TCGTGCTCGC | AGGGCTCTCA | CCCTTGACTC | TTTTAATAGC | 240 |
| TCTTCTGTGC | AAGATTACAA | TCTAAACAAT | TCGGAGAACT | CGACCTTCCT | CCTGAGGCAA | 300 |
| GGACCACAGC | CAACTTCCTC | TTACAAGCCG | CATCGATTTT | GTCCTTCAGA | AATAGAAATA | 360 |
| AGAATGCTTG | CTAAAAATTA | TATTTTTACC | AATAAGACCA | ATCCAATAGG | TAGATTATTA | 420 |
| GTTACTATGT | TAAGAAATGA | ATCATTATCT | TTTAGTACTA | TTTTTACTCA | AATTCAGAAG | 480 |
| TTAGAAATGG | GAATAGAAAA | TAGAAAGAGA | CGCTCAACCT | CAATTGAAGA | ACAGGTGCAA | 540 |
| GGACTATTGA | CCACAGGCCT | AGAAGTAAAA | AAGGGAAAAA | AGAGTGTTTT | TGTCAAAATA | 600 |
| GGAGACAGGT | GGTGGCAACT | AGGGACTTAT | AGGGGACCTT | ACATCTACAG | ACCAACAGAT | 660 |
| GCCCCCTTAC | CATATACAGG | AAGATATGAC | TTAAATTGGG | ATAGGTGGGT | TACAGTCAAT | 720 |
| GGCTATAAAG | TGTTATATAG | ATCCCTCCCT | TTTCGTGAAA | GACTCGCCAG | AGCTAGACCT | 780 |
| CCTTGGTATA | TGTTGTCTCA | AGAAGAAAAA | GACGACATGA | AACAACAGGT | ACATGATTAT | 840 |
| ATTTATCTAG | GAACAAGAAT | GCACTTTTGG | GGAAAGATTT | CCATACCAAG | GAGGGGACAG | 900 |
| TGGCTAGACA | ATAGAACATT | ATTCTACAAA | AACTTATGAC | ATGAGTTATT | ATAAATAGCC | 960 |

-continued

| | | | | | | |
|---|---|---|---|---|---|---|
| TTTATTGGCC | CAACCTTGCG | GTTCCCAGGG | CTTAGTAAGT | TTTGGTTAC | AAACTGTTCT | 1020 |
| TAAAACGAGG | ATGTGACTCC | TATGTTCTTT | GGAACGGTTC | CCAGGGCTTA | AGTAAGTTTT | 1080 |
| TGGTTACAAA | CTATTCTTAA | AACGAGGATG | TGACTCCTAT | GTTCTTTTGG | ACGGTTCCCA | 1140 |
| GGGCTTAAGT | AAGTTTTTGG | TTACAAACTG | TTCTTAAAAC | GAGGATGTGA | CTCCTATGTT | 1200 |
| CTTTTGGAAC | GCTTAAGTAA | GCTTAAGTAA | GTTTTTGGTT | ACAAACTGTT | CTTAAAACGA | 1260 |
| GGATGTGAGA | CAAGTGGTTT | CCTGACTTGG | TTTGGTATCA | AAGGTTCTGA | TCTGAGCTCT | 1320 |
| GAGTGTTCTA | TTTTCCTATG | TTCTTTTGGA | ATTTATCCAA | ATCTTATGTA | AATGCTTATG | 1380 |
| TAAACCAAGA | TATAAAAGAG | TGCTGATTTT | TTTGAGTAAA | CTTGCAACAG | TTCCTAACAT | 1440 |
| TCACCTCTTG | TGTGTTTGTG | TCTGTTCGCC | ATCCCGTCTC | CGCTCGTCAC | TTATCCTTCA | 1500 |
| CTTTCCTGCG | GGTCCCCCCG | CAGACCCGG | CGACCTCAGG | TCGGCCGACT | GCGGCAGCTG | 1560 |
| GCGCCCGAAC | AGGGACCCCT | CGGATAAGTG | ACCCTTGTCT | CTATTTCTAC | TATTTGGTGT | 1620 |
| TTGTCTTGTA | TTGTCTCTTT | CTTGTCTTTC | TATCATCACA | AGAGCGGAAC | GGACTCACCA | 1680 |
| TAGGGAGCTG | CAG | | | | | 1693 |

( 2 ) INFORMATION FOR SEQ ID NO:15:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 9
        ( D ) OTHER INFORMATION: /note= "Nucleotide 9 is N wherein N
            = ( U / C )."

( i x ) FEATURE:
        ( A ) NAME/KEY: misc_feature
        ( B ) LOCATION: 10
        ( D ) OTHER INFORMATION: /note= "Nucleotide 10 is N wherein
            N =N11."

( x i ) SEQUENCE DESCRIPTION: SEQ ID NO:15:

AGGUAAGUNN CAGG            14

( 2 ) INFORMATION FOR SEQ ID NO:16:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

GCCGCCAGCC AUGG            14